(12) United States Patent
Shoda

(10) Patent No.: US 7,935,720 B2
(45) Date of Patent: May 3, 2011

(54) CRYSTAL OF SUBSTITUTED PHENYLALKANOIC ACID ESTER AND PROCESS FOR PRODUCING THE SAME

(75) Inventor: Motoshi Shoda, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 12/898,367

(22) Filed: Oct. 5, 2010

(65) Prior Publication Data

US 2011/0021593 A1    Jan. 27, 2011

Related U.S. Application Data

(60) Continuation of application No. 12/788,061, filed on May 26, 2010, now Pat. No. 7,838,546, which is a division of application No. 12/483,814, filed on Jun. 12, 2009, now Pat. No. 7,754,752, which is a division of application No. 11/826,999, filed on Jul. 19, 2007, now Pat. No. 7,560,478.

(60) Provisional application No. 60/832,406, filed on Jul. 20, 2006.

(30) Foreign Application Priority Data

Jul. 20, 2006    (JP) .................................. 2006-197637

(51) Int. Cl.
*A61K 31/416*    (2006.01)
*C07D 231/56*    (2006.01)
(52) U.S. Cl. .................................... 514/403; 548/361.1
(58) Field of Classification Search .................. 514/403; 548/361.1
See application file for complete search history.

(56) References Cited

U.S. PATENT DOCUMENTS

| | | |
|---|---|---|
| 2004/0044258 A1 | 3/2004 | Shoda et al. |
| 2004/0235817 A1 | 11/2004 | Brands et al. |
| 2005/0032787 A1 | 2/2005 | Giannessi et al. |
| 2006/0276525 A1 | 12/2006 | Adin et al. |

FOREIGN PATENT DOCUMENTS

| | | |
|---|---|---|
| CN | 1653032 A | 8/2005 |
| EP | 0 470 832 A2 | 2/1992 |
| EP | 0 473 308 A1 | 3/1992 |
| EP | 1 024 130 A1 | 8/2000 |
| EP | 1 323 701 A1 | 7/2003 |
| EP | 1 477 472 A1 | 11/2004 |
| WO | WO 03/070686 A1 | 8/2003 |
| WO | WO 2005/016862 A1 | 2/2005 |

OTHER PUBLICATIONS

EP 07 79 0690, European Search Report, Aug. 11, 2010, 7 pages.
Additional Information Regarding Properties of 3-[3-amino-4(indian-2-yloxy)-5-1-(1-methyl-1H-indazol-5-yl)phenyl]propionic acid Made Under Different Conditions, Dec. 11, 2008.
Brittain et al., Polymorphism in Pharmaceutical Solids, vol. 95, 1999, p. 228-229.
Byrn et al., Solid-State Chemistry of Drugs, 1999, SSCI, Inc., Second Edition, pp. 62-63.
CA 2,659,471; Office Action, Jul. 5, 2010, pp. 1-3.
Chawla et al., Challenges in Polymorphism of Pharmaceuticals, CRIPS, vol. 5, No. 1, Jan.-Mar. 2004, pp. 9-12.
Mino R. Caira, "Crystalline Polymorphism of Organic Compounds," Topics in Current Chemistry, vol. 198, Jan. 1, 1998, pp. 163-208, XP001156954.
Newman et al., Solid-State analysis of the active pharmeceutical ingredient in drug products, DDT, vol. 8, No. 19, Oct. 2003, pp. 898-905.

*Primary Examiner* — Kamal A Saeed
*Assistant Examiner* — Kristin Bianchi
(74) *Attorney, Agent, or Firm* — Birch, Stewart, Kolasch & Birch, LLP

(57) ABSTRACT

In the case of using 3-[3-amino-4-(indan-2-yloxy)-5-(1-methyl-1H-indazol-5-yl)phenyl]propionic acid, methyl 3-[4-(indan-2-yloxy)-3-(1-methyl-1H-indazol-5-yl)-5-nitrophenyl]propionate, or methyl 3-[3-amino-4-(indan-2-yloxy)-5-(1-methyl-1H-indazol-5-yl)phenyl]propionate as a medicine, more preferable aspects or improved methods are provided.
Crystals of any compound among 3-[3-amino-4-(indan-2-yloxy)-5-(1-methyl-1H-indazol-5-yl)phenyl]propionic acid, methyl 3-[4-(indan-2-yloxy)-3-(1-methyl-1H-indazol-5-yl)-5-nitrophenyl]propionate, and methyl 3-[3-amino-4-(indan-2-yloxy)-5-(1-methyl-1H-indazol-5-yl)phenyl]propionate, and methods of producing the same are provided.

5 Claims, 12 Drawing Sheets

CRYSTAL OF SUBSTITUTED PHENYLALKANOIC ACID ESTER AND PROCESS FOR PRODUCING THE SAME

CROSS REFERENCE TO RELATED APPLICATIONS

This application is a Continuation of application Ser. No. 12/788,061 filed on May 26, 2010 now U.S. Pat. No. 7,838,546, which is a Divisional of application Ser. No. 12/483,814 filed on Jun. 12, 2009, which has issued as U.S. Pat. No. 7,754,752 B2 and issued on Jul. 13, 2010, which is a Divisional of application Ser. No. 11/826,999 filed on Jul. 19, 2007, which has issued as U.S. Pat. No. 7,560,478 B2 and issued on Jul. 14, 2009, and for which priority is claimed under 35 U.S.C. §120; and this application claims priority of Application No. 2006-197637 filed in Japan on Jul. 20, 2006 and U.S. Provisional Application No. 60/832,406, filed on Jul. 20, 2006 under 35 U.S.C. §119; the entire contents of all are hereby incorporated by reference.

TECHNICAL FIELD

The present invention relates to novel crystals. More particularly, the invention relates to novel crystals of any of compounds 3-[3-amino-4-(indan-2-yloxy)-5-(1-methyl-1H-indazol-5-yl)phenyl]propionic acid, methyl 3-[4-(indan-2-yloxy)-3-(1-methyl-1H-indazol-5-yl)-5-nitrophenyl]propionate, and methyl 3-[3-amino-4-(indan-2-yloxy)-5-(1-methyl-1H-indazol-5-yl)phenyl]propionate, or a method of producing the crystals.

BACKGROUND ART

3-[3-Amino-4-(indan-2-yloxy)-5-(1-methyl-1H-indazol-5-yl)phenyl]propionic acid is reported to have a prostaglandin production suppressing effect and a leukotriene production suppressing effect, and thus the usefulness of the compound in the prophylaxis and/or treatment of various inflammatory diseases caused by lipid mediators, autoimmune diseases, allergic diseases or pain, and methods of producing such compound are disclosed.

[Patent Document 1] WO 03/70686

DISCLOSURE OF THE INVENTION

Problems to be Solved by the Invention

It is an object of the invention to provide a preferred aspect or a method for improvement when using the compound of the present invention as a medicine.

Means for Solving the Problems

Compound 1 of the present invention, 3-[3-amino-4-(indan-2-yloxy)-5-(1-methyl-1H-indazol-5-yl)phenyl]propionic acid (hereinafter, may be referred to as "Compound 1 of the invention"), is obtained, according to the above-described known production method, by adding a 2 N aqueous solution of sodium hydroxide to a methanol solution of methyl 3-[3-amino-4-(indan-2-yloxy)-5-(1-methyl-1H-indazol-5-yl)phenyl]propionate, stirring the mixture solution at 60° C. for 16 hours, concentrating the reaction mixture under reduced pressure, acidifying the reaction mixture with a 5% aqueous hydrochloric acid solution under ice cooling, extracting the reaction mixture with ethyl acetate, washing the organic layer with saturated brine, drying and then distilling off the solvent under reduced pressure. According to this known production method, the compound of the invention is obtained as a colorless to brown oily matter. The inventors of the present invention conceived that upon administering the Compound 1 of the invention as a medicine, new improvement was required in order to further facilitate the handling. Thus, the inventors conducted extensive research and confirmed that the Compound 1 of the invention is crystallized, thus completing the present invention.

According to the present invention, since crystals of the Compound 1 of the invention are provided, handling in the formulation processes becomes easy, and it is easy to make the content of the compound of the invention constant in each preparation, which points are highly preferred. Furthermore, the crystals of the compounds of the invention also allow, in view of removing solvents and the like, easy and more complete removal of solvents and the like compared to the case of an oily matter. The crystals are also appropriate for the production in an industrial scale, and it is highly preferred.

In addition, the inventors of the present invention further conducted investigation on the above-mentioned crystals, and as a result, found that the Compound 1 of the invention exists in the forms of type A crystals and type B crystals, which are new and show the properties that will be described later, and that the crystals of two types respectively show preferred properties. The inventors further established a method of selectively obtaining such crystals, and thus completed the present invention.

In addition, according to the known production method described above, methyl 3-[4-(indan-2-yloxy)-3-(1-methyl-1H-indazol-5-yl)-5-nitrophenyl]propionate (hereinafter, may be referred to as "Compound 2 of the invention") is obtained by adding a 2 M aqueous solution of sodium carbonate, toluene and tetrakistriphenylphosphine palladium(0) to an ethanol solution of methyl 3-(3-bromo-4-hydroxy-5-nitrophenyl)propionate and 1-methyl-1H-indazole-5-boric acid, stirring the mixture solution at 80° C. for 16 hours, subsequently adding ethyl acetate to the reaction mixture, washing the reaction mixture sequentially with a saturated aqueous solution of sodium bicarbonate, a saturated aqueous solution of ammonium chloride and saturated brine, drying the organic layer, then distilling off the solvent under reduced pressure, and purifying the residue by flash column chromatography. With regard to this known production method, nothing is mentioned about the form of the compounds of the invention. According to this known production method, it cannot be necessarily said that handling during the production is easy. Also, the inventors of the present invention confirmed that in the case of using the Compound 2 of the invention as a medicine, there occur problems in making the medicine with a constant content of the compound, facilitating the removal of solvent, and the like. The inventors also confirmed that the Compound 2 of the invention can be obtained in a novel crystal form, and thus completed the present invention.

Moreover, according to the above-described known production method, methyl 3-[3-amino-4-(indan-2-yloxy)-5-(1-methyl-1H-indazol-5-yl)phenyl]propionate (hereinafter, may be referred to as "Compound 3 of the invention"; further, the "Compound 1 of the invention", "Compound 2 of the invention" and "Compound 3 of the invention" may be collectively referred to as "compounds of the invention") is obtained by adding Raney 2800 nickel to an ethyl acetate/methanol solution of the Compound 2 of the invention described above, stirring the reaction mixture in a hydrogen atmosphere at room temperature for 6 hours, subsequently filtering the reaction mixture, distilling off the solvent of the filtrate under reduced pressure, and then purifying the residue by column chromatography. In this known production method, nothing is mentioned about the form of the Compound 3 of the invention, but it cannot be necessarily said that handling is easy during the production. Also, the inventors of the present invention confirmed that in the case of using the Compound 3 of the invention as a medicine, there are problems in making the medicine with a constant content of the compound, facilitating the removal of solvent, and the like, and thus completed the present invention.

Thus, the present invention is as follows.

(1) A crystal of any of 3-[3-amino-4-(indan-2-yloxy)-5-(1-methyl-1H-indazol-5-yl)phenyl]propionic acid, methyl 3-[4-(indan-2-yloxy)-3-(1-methyl-1H-indazol-5-yl)-5-nitrophenyl]propionate, and methyl 3-[3-amino-4-(indan-2-yloxy)-5-(1-methyl-1H-indazol-5-yl)phenyl]propionate.

(2) A crystal of 3-[3-amino-4-(indan-2-yloxy)-5-(1-methyl-1H-indazol-5-yl)phenyl]propionic acid.

(3) A crystal of methyl 3-[4-(indan-2-yloxy)-3-(1-methyl-1H-indazol-5-yl)-5-nitrophenyl]propionate.

(4) A crystal of methyl 3-[3-amino-4-(indan-2-yloxy)-5-(1-methyl-1H-indazol-5-yl)phenyl]propionate.

(5) The crystal according to (1) or (2) above, wherein the crystal is a type A crystal of 3-[3-amino-4-(indan-2-yloxy)-5-(1-methyl-1H-indazol-5-yl)phenyl]propionic acid having at least one or more characteristic peaks at 2θ selected from 6.9±0.2°, 16.4±0.2°, 18.2±0.2°, 25.0±0.2° and 27.5±0.2° in a powder X-ray diffraction spectrum.

Additionally, the 2θ angle in the powder X-ray diffraction spectrum may have some measurement error that is allowable, due to various factors, and the corresponding actual measurement values have fluctuations of usually ±0.3°, typically ±0.2°, and about ±0.1° for more preferable measurements. Therefore, it should be understood that in the present specification, the 2θ angle for a specific sample obtained on the basis of the actual measurement values may include such allowable error.

(5-1) The crystal according to (1), (2) or (5) above, wherein the crystal is a type A crystal of 3-[3-amino-4-(indan-2-yloxy)-5-(1-methyl-1H-indazol-5-yl)phenyl]propionic acid having characteristic peaks at 2θ of 6.9±0.2°, 14.4±0.2°, 16.4±0.2°, 18.2±0.2°, 25.0±0.2° and 27.5±0.2° in a powder X-ray diffraction spectrum.

(6) The crystal according to (1), (2), (5) or (5-1) above, wherein the crystal is a type A crystal of 3-[3-amino-4-(indan-2-yloxy)-5-(1-methyl-1H-indazol-5-yl)phenyl]propionic acid having an endothermic peak at about 182° C. in a differential scanning calorimetric analysis (heating rate: 10° C./min).

Additionally, the endothermic peak in the differential scanning calorimetric analysis is an intrinsic property that are inherent to the crystals of the compounds of the invention, but it cannot be denied that in the actual measurement, there is a possibility to have fluctuation in the melting point, which is attributable to the experimental error, as well as the incorporation of an optionally allowable amount of impurities and the like. Therefore, a person having ordinary skill in the art would sufficiently understand to what extent the actual measurement values of the endothermic peak temperature in the present invention may fluctuate, and for example, there is expected an error of usually about ±5°, typically about ±3°, and about ±2° for preferable measurements.

(7) The crystal according to any of (1), (2), (5), (5-1) and (6) above, wherein the crystal is a type A crystal of 3-[3-amino-4-(indan-2-yloxy)-5-(1-methyl-1H-indazol-5-yl)phenyl]propionic acid having conspicuous infrared absorption bands around wavenumbers of 3361, 2938, 1712, 1204, 1011 and 746 $cm^{-1}$ in an infrared absorption spectrum.

It should be noted that some measurement error is allowed in the infrared absorption spectrum wavenumber, and it is conceived that the present invention may also include this error. A person having ordinary skill in the art would sufficiently understand the extent of the error, and for example, upon referring to the $4^{th}$ edition of the European Pharmacopoeia, it is marked that in a confirmation test by means of infrared absorption spectrum, the data should be consistent within ±0.5% of the wavenumber scale, when compared with the reference spectrum. According to the present invention, there is no particular limitation, but such conventionally conceived range of error may be considered, and for example, as a measure, a change of about ±0.8%, preferably about ±0.5%, and particularly preferably about ±0.2% may be exemplified for the actual measurement values in the wavenumber scale.

(7-1) Type, A crystal of 3-[3-amino-4-(indan-2-yloxy)-5-(1-methyl-1H-indazol-5-yl)phenyl]propionic acid according to any of (5) to (7) above, wherein the crystal purity is at least 90% by weight or greater.

Additionally, it is meant by (5) to (7) in the above-described sentence that the inventions under the subtitle numbers following the order of disposition are also included, and specifically, the term means to include (5), (5-1), (6) and (7). The same applies throughout the following.

(8) The crystal according to (1) or (2), wherein the crystal is a type B crystal of 3-[3-amino-4-(indan-2-yloxy)-5-(1-methyl-1H-indazol-5-yl)phenyl]propionic acid having at least one or more characteristic peaks at 2θ selected from 15.9±0.2°, 17.3±0.2°, 22.2±0.2° and 22.9±0.2° in a powder X-ray diffraction spectrum.

(8-1) The crystal according to (1), (2) or (8) above, wherein the crystal is a type B crystal of 3-[3-amino-4-(indan-2-yloxy)-5-(1-methyl-1H-indazol-5-yl)phenyl]propionic acid having characteristic peaks at 2θ of 14.4±0.2°, 15.9±0.2°, 17.3±0.2°, 22.2±0.2° and 22.9±0.2° in a powder X-ray diffraction spectrum.

(9) The crystal according to (1), (2) (8) or (8-1) above, wherein the crystal is a type B crystal of 3-[3-amino-4-(indan-2-yloxy)-5-(1-methyl-1H-indazol-5-yl)phenyl]propionic acid having an endothermic peak at about 203° C. in a differential scanning calorimetric analysis (heating rate: 10° C./min).

(10) The crystal according to (1), (2), (8), (8-1) or (9) above, wherein the crystal is a type B crystal of 3-[3-amino-4-(indan-2-yloxy)-5-(1-methyl-1H-indazol-5-yl)phenyl] propionic acid having conspicuous infrared absorption bands around wavenumbers of 2939, 1720, 1224, 1016 and 751 $cm^{-1}$ in an infrared absorption spectrum.

(10-1) Type B crystal of 3-[3-amino-4-(indan-2-yloxy)-5-(1-methyl-1H-indazol-5-yl)phenyl]propionic acid according to any of (8) to (10) above, wherein the crystal purity is at least 90% by weight or greater.

(10-2) The crystal according to (1) or (3) above, wherein the crystals is a crystal of methyl 3-[4-(indan-2-yloxy)-3-(1-methyl-1H-indazol-5-yl)-5-nitrophenyl]propionate having at least one or more characteristic peaks at 2θ selected from 7.6±0.2°, 15.3±0.2°, 18.0±0.2°, 21.3±0.2° and 26.9±0.2° in a powder X-ray diffraction spectrum.

(10-3) The crystal according to (1), (3) or (10-2) above, wherein the crystal is a crystal of methyl 3-[4-(indan-2-yloxy)-3-(1-methyl-1H-indazol-5-yl)-5-nitrophenyl]propionate having characteristic peaks at 2θ of 7.6±0.2°, 15.3±0.2°, 18.0±0.2°, 21.3±0.2° and 26.9±0.2° in a powder X-ray diffraction spectrum.

(10-4) The crystal according to (1) or (4) above, wherein the crystal is a crystal of methyl 3-[3-amino-4-(indan-2-yloxy)-5-(1-methyl-1H-indazol-5-yl)phenyl]propionate having at least one or more characteristic peaks at 2θ selected from 8.6±0.2°, 12.7±0.2°, 17.2±0.2°, 17.6±0.2°, 18.9±0.2° and 21.0±0.2° in a powder X-ray diffraction spectrum.

(10-5) The crystal according to (1), (4) or (10-4) above, wherein the crystal is a crystal of methyl 3-[3-amino-4-(indan-2-yloxy)-5-(1-methyl-1H-indazol-5-yl)phenyl]propionate having characteristic peaks at 2θ of 8.6±0.2°, 12.7±0.2°, 17.2±0.2°, 17.6±0.2°, 18.9±0.2° and 21.0±0.2° in a powder X-ray diffraction spectrum.

(11) A pharmaceutical composition comprising any of the crystals of 3-[3-amino-4-(indan-2-yloxy)-5-(1-methyl-1H-indazol-5-yl)phenyl]propionic acid, or a type A crystal or a type B crystal thereof, the crystals of methyl 3-[4-(indan-2-yloxy)-3-(1-methyl-1H-indazol-5-yl)-5-nitrophenyl]propionate, and the crystals of methyl 3-[3-amino-4-(indan-2-yloxy)-5-(1-methyl-1H-indazol-5-yl)phenyl]propionate according to any of (1) to (10-5) above, as an active ingredient, and a pharmaceutically acceptable carrier.

(12) The pharmaceutical composition according to (11) above, wherein the pharmaceutically acceptable carrier is a dry product, and the pharmaceutical composition is a dry preparation.

(13) A pharmaceutical composition comprising, as an active ingredient, a type A crystal of 3-[3-amino-4-(indan-2-yloxy)-5-(1-methyl-1H-indazol-5-yl)phenyl]propionic acid according to any of (5) to (7) above, wherein the crystal purity of the type A crystal is at least 90% by weight or greater and a pharmaceutically acceptable carrier.

(14) A pharmaceutical composition comprising, as an active ingredient, a type B crystal of 3-[3-amino-4-(indan-2-yloxy)-5-(1-methyl-1H-indazol-5-yl)phenyl]propionic acid according to any of (8) to (10) above, wherein the crystal purity of the type B crystal is at least 90% by weight or greater and a pharmaceutically acceptable carrier.

(15) A method of producing a type A crystal of 3-[3-amino-4-(indan-2-yloxy)-5-(1-methyl-1H-indazol-5-yl)phenyl] propionic acid according to any of (5) to (7-1) above, the method comprising adding an acid to a basic solution of 3-[3-amino-4-(indan-2-yloxy)-5-(1-methyl-1H-indazol-5-yl)phenyl]propionic acid to produce crystals of 3-[3-amino-4-(indan-2-yloxy)-5-(1-methyl-1H-indazol-5-yl)phenyl] propionic acid, and obtaining the crystals.

(16) The method of producing a type A crystal of 3-[3-amino-4-(indan-2-yloxy)-5-(1-methyl-1H-indazol-5-yl)phenyl]propionic acid, according to (15) above, wherein the basic solution of 3-[3-amino-4-(indan-2-yloxy)-5-(1-methyl-1H-indazol-5-yl)phenyl]propionic acid is an alkali hydrolysate of a lower alkyl ester of 3-[3-amino-4-(indan-2-yloxy)-5-(1-methyl-1H-indazol-5-yl)phenyl]propionic acid.

(16-1) A method of producing a type A crystal of 3-[3-amino-4-(indan-2-yloxy)-5-(1-methyl-1H-indazol-5-yl)phenyl]propionic acid according to any of (5) to (7-1) above, the method comprising adding an acid to the reaction solution obtained after an alkali hydrolysis reaction of a lower alkyl ester of 3-[3-amino-4-(indan-2-yloxy)-5-(1-methyl-1H-indazol-5-yl)phenyl]propionic acid, thus to produce the crystals of 3-[3-amino-4-(indan-2-yloxy)-5-(1-methyl-1H-indazol-5-yl)phenyl]propionic acid, and obtaining the crystals.

(17) A method of producing a type B crystal of 3-[3-amino-4-(indan-2-yloxy)-5-(1-methyl-1H-indazol-5-yl)phenyl] propionic acid according to any of (8) to (10-1) above, the method comprising crystallizing 3-[3-amino-4-(indan-2-yloxy)-5-(1-methyl-1H-indazol-5-yl)phenyl]propionic acid from a solution having 3-[3-amino-4-(indan-2-yloxy)-5-(1-methyl-1H-indazol-5-yl)phenyl]propionic acid dissolved in any one or two or more solvents selected from the group consisting of acetone, dichloromethane, methanol, ethyl acetate, methanol/acetic acid mixture solution, and acetonitrile.

(18) A method of producing a crystal according to any of (8) to (10-1) above, the method comprising adding an acid to a basic solution of 3-[3-amino-4-(indan-2-yloxy)-5-(1-methyl-1H-indazol-5-yl)phenyl]propionic acid, then adding type B crystals of the compound as seed crystals immediately before crystallization taking place by the addition of the acid, whereby the type B crystals of 3-[3-amino-4-(indan-2-yloxy)-5-(1-methyl-1H-indazol-5-yl)phenyl]propionic acid are formed.

(18-1) The method of producing a type B crystal of 3-[3-amino-4-(indan-2-yloxy)-5-(1-methyl-1H-indazol-5-yl)phenyl]propionic acid, according to (18) above, wherein the basic solution of 3-[3-amino-4-(indan-2-yloxy)-5-(1-methyl-1H-indazol-5-yl)phenyl]propionic acid is an alkali hydrolysate of a lower alkyl ester of 3-[3-amino-4-(indan-2-yloxy)-5-(1-methyl-1H-indazol-5-yl)phenyl]propionic acid.

(18-2) A method of producing a crystal according to any of (8) to (10-1) above, the method comprising adding an acid to the reaction solution obtained after an alkali hydrolysis reaction of a lower alkyl ester of 3-[3-amino-4-(indan-2-yloxy)-5-(1-methyl-1H-indazol-5-yl)phenyl]propionic acid, then adding type B crystals of the compound as seed crystals to the reaction solution immediately before crystallization taking place by the addition of the acid, whereby the type B crystals of 3-[3-amino-4-(indan-2-yloxy)-5-(1-methyl-1H-indazol-5-yl)phenyl]propionic acid are formed.

(19) A method of producing crystals of methyl 3-[4-(indan-2-yloxy)-3-(1-methyl-1H-indazol-5-yl)-5-nitrophenyl]propionate, the method comprising adding any one or two or more solvents selected from the group consisting of heptane, diisopropyl ether, isopropanol, t-butyl methyl ether and water, to a solution of methyl 3-[4-(indan-2-yloxy)-3-(1-methyl-1H-indazol-5-yl)-5-nitrophenyl]propionate dissolved in any one or two or more solvents selected from the group consisting of toluene, ethyl acetate, tetrahydrofuran, acetone, dimethoxyethane and methanol, thus to produce crystals.

(19-1) The method according to (19) above, wherein the crystals are crystals having at least one or more characteristic peaks, and typically all of the peaks, at 2θ of 7.6±0.2°, 15.3±0.2°, 18.0±0.2°, 21.3±0.2° and 26.9±0.2° in a powder X-ray diffraction spectrum.

(20) A method of producing crystals of methyl 3-[3-amino-4-(indan-2-yloxy)-5-(1-methyl-1H-indazol-5-yl)phenyl] propionate, the method comprising adding any one or two or more solvents selected from the group consisting of heptane, isopropanol, methanol and water, to a solution of methyl 3-[3-amino-4-(indan-2-yloxy)-5-(1-methyl-1H-indazol-5-yl)phenyl]propionate dissolved in any one or two or more solvents selected from the group consisting of toluene, ethyl acetate, tetrahydrofuran and acetone, thus to produce crystals.

(20-1) The method according to (20) above, wherein the crystals are crystals having at least one or more characteristic peaks, and typically all of the peaks, at 2θ of 8.6±0.2°, 12.7±0.2°, 17.2±0.2°, 17.6±0.2°, 18.9±0.2° and 21.0±0.2° in a powder X-ray diffraction spectrum.

The crystals of Compound 1 of the invention are highly advantageous in the formulation processes, from the viewpoints that it is easy to make the content of the compound of the invention constant in each preparation, and the like. Further, the crystals are also favorable from the viewpoint that it is easy to remove solvents and the like therefrom, compared to the case of oily matter, thus being suitable for the production in an industrial scale.

As the crystals of the Compound 1 of the invention used in certain aspects of the present invention, type A crystal may be favorably mentioned. The type A crystal of the Compound 1 of the invention is a crystal defined by any one or two or more combinations of various properties described in the above-described inventions (5) to (7-1), or of various properties confirmed in Examples, Test Examples and the like of the present specification. From the fact that this type A crystal exhibits certain properties, in addition to the advantages possessed by the crystals of the Compound 1 of the invention described above, it was confirmed that the type A crystal exhibits preferred properties as a preparation or in manifesting a drug action, and in the production processes, as compared to simple, uncontrolled crystals. In addition, the type A crystal described above is recognized to have higher solubility in aqueous solvents, for example, compared to the type B crystal that will be described later, and is therefore preferred in that point.

To maximally manifest the preferred effects possessed by the type A crystal, it is preferable to use crystals which are substantially type A crystals, and as such form of the type A crystals, type A crystals having a crystal purity (in percent) is usually about 90% by weight or greater may be mentioned, and such crystals having a crystal purity of preferably 95% by weight or greater, more preferably 97% by weight or greater, even more preferably 99% by weight or greater, and particularly preferably about 100% by weight, may be mentioned. Also, in some cases, a crystal purity of 93% by weight or greater is preferred, that of 98% by weight or greater is more preferred, and that of 99.5% by weight or greater is particularly preferred. Furthermore, in the case of using the crystals as a medicine of the invention, usually a crystal purity of 80% by weight or greater may also be favorable. Furthermore, as a preferred aspect of the type A crystals, crystals substantially not containing any crystal type other than type A may be mentioned. The term "substantially not containing" means that the crystals contain any crystal types other than the type A crystal preferably in an amount of 10% by weight or less, more preferably 5% by weight or less, still more preferably 3% by weight or less, and particularly preferably 1% by weight or less, and most preferably do not contain any other crystal types at all.

As the crystals used in another aspect of the present invention, type B crystal may also be mentioned as a preferred example. The type B crystal of the Compound 1 of the invention is a crystal defined by any one or two or more combinations of various properties described in the above-described inventions (8) to (10-1), or various properties confirmed in Examples, Test Examples and the like of the present specification. From the fact that this type B crystal exhibits certain properties, in addition to the advantages possessed by the crystals of the Compound 1 of the invention described above, it was confirmed that the type B crystal exhibits preferred properties as a preparation or in manifesting a drug action, and in the production processes, as compared to simple, uncontrolled crystals. Furthermore, this type B crystal has higher filterability compared to the type A crystal, and besides, has more improved flow properties, and thus in the case of mass-producing the type B crystals, for example, it is expected that the time taken in the filtration process and/or dehydration process can be shortened. Also, the type B crystal is more preferred in the case of producing dry preparations or solid preparations. It was confirmed that the type B crystal after filtration and dehydration has lower water content than the type A crystal after filtration and dehydration, and thus it is expected and considered to be preferred, particularly in the case of mass production, to shorten the time taken in drying or reduce the heat energy. Apart from this, this type B crystal is believed to have substantially more favorable morphological stability than the type A crystal. In order to maximally manifest the effects possessed by the type B crystal, it is preferable to use crystals which are substantially type B crystals, and as such form of the type B crystals, type B crystals having a crystal purity (in percent) is usually about 90% by weight or greater may be mentioned, and such crystals having a crystal purity of preferably 95% by weight or greater, more preferably 97% by weight or greater, even more preferably 99% by weight or greater, and particularly preferably about 100% by weight, may be mentioned. Also, in some cases, a crystal purity of 93% by weight or greater is preferred, that of 98% by weight or greater is more preferred, and that of 99.5% by weight or greater is particularly preferred. Furthermore, in the case of using the crystals as a medicine of the invention, usually a crystal purity of 80% by weight or greater may also be favorable. Furthermore, as a preferred aspect of the type B crystals, crystals substantially not containing any crystal type other than type B may be mentioned. The term "substantially not containing" means that the crystals contain any crystal types other than the type B crystal preferably in an amount of 10% by weight or less, more preferably 5% by weight or less, still more preferably 3% by weight or less, and particularly preferably 1% by weight or less, and most preferably do not contain any other crystal types at all.

Additionally, the crystal purity (in percent) of the type A crystal may be calculated by dividing the weight of type A crystals by the total weight of the Compound 1 of the invention containing the type A crystals, and multiplying the resultant by 100. Herein, as the method for measuring the weight of the type A crystals, or the weight of presence of the Compound 1 of the invention, any of the following methods may be applied, which may be further modified as appropriate.

Moreover, there may be cases where measurement errors appear more excessively than necessary, depending on the measurement method, but in that case, it is preferable to check the size of the error using standard materials of known amounts, and correct the error. For example, according to the present invention, it is particularly preferable to indicate the crystal purity using a value which is calculated by dividing the measured value for the crystal obtained by the measurement with the differential scanning calorimetric analysis (in particular, the specific measurement conditions described in the present specification may be mentioned as particularly preferable examples), by the measured value for the Compound 1 of the invention obtained by the measurement by means of HPLC (in particular, the specific measurement conditions described in the present specification may be mentioned as particularly preferable examples), and multiplying the resultant by 100. Furthermore, the same method as described in the above may also apply to the determination of the crystal purity (in percent) of the type B crystal, though appropriate modifications can be made to the measurement methods. Specifically, it is particularly preferable to indicate the crystal purity using a value which is calculated by dividing the measured value for the crystal obtained by the measurement with the differential scanning calorimetric analysis (in particular, the specific measurement conditions described in the present specification may be mentioned as particularly preferable examples), by the measured value for the Compound 1 of the invention obtained by the measurement by means of HPLC (in particular, the specific measurement conditions described in the present specification may be mentioned as particularly preferable examples), and multiplying the resultant by 100.

In summary, amount of each crystal can be calculated by measuring the intensities of characteristic peaks in the differential scanning calorimetric analysis, powder X-ray diffraction spectrum, infrared absorption spectrum, solid $^{13}$C-NMR spectrum, Raman spectrum and the like, and particularly in the case of measuring the ratio of presence between the type A crystal and the type B crystal of the Compound 1 of the invention as described above, the method of measuring the amounts by differential scanning calorimetric analysis may be mentioned as a preferred example. In a specific method to determine the amount of the type A crystal of the Compound 1 of the invention with using a differential scanning calorimetric analysis employing a suitable heating rate (as the suitable heat rate, for example, 50° C./min may be mentioned), pure type A crystals are used as the crystal standard material and a calibration curve is prepared by plotting the weight (mg) of the standard material against the area of the endothermic peak (mJ) near around 185° C. which indicates the melting of the type A crystals. Thereafter, the area of the endothermic peak (mJ) near around 185° C. measured for the sample is compared with the calibration curve described above. Then, the amount of the type A crystal can be calculated. Also, for the type B crystal of the Compound 1 of the invention, the amount can be calculated in the same manner. That is, using pure type B crystals as the crystal standard material, the endothermic peak area near around 205° C. for example, may be usually measured as the endothermic peak for the type B crystal in differential scanning calorimetric analysis.

Also in measurement methods other than differential scanning calorimetric analysis, namely, the measurement methods such as powder X-ray diffraction spectrum, infrared absorption spectrum, solid $^{13}$C-NMR spectrum and Raman spectrum, the amount of the crystals of desired type can be calculated by preparing a calibration curve in the same manner as in differential scanning calorimetric analysis, using a standard material.

In particular, in the case of determining the amount of the crystals of desired type by a measurement method other than differential scanning calorimetric analysis, namely, powder X-ray diffraction spectrum, infrared absorption spectrum, solid 13C-NMR spectrum, Raman spectrum or the like, a calibration curve can be prepared by appropriately selecting peaks that are characteristic to the respective crystal types, and the amount of presence of the crystals of desired type can be calculated.

Furthermore, as the optical system used in the powder x-ray diffraction spectrometric measurement, an optical system for general focusing method, or an optical system for parallel beam method may be exemplified. The optical system to be used is not particularly limited, but when it is desirable to secure the resolution or intensity, it is preferable to perform measurement using an optical system for focusing method. Also, when it is desirable to suppress orientation, which is a phenomenon that crystals are directed to a certain direction due to the crystal shape (needle shape, plate shape, etc.), it is preferable to perform measurement using an optical system for parallel beam method. As the measurement apparatus for the optical system for focusing method, XRD-6000 (SHIMADZU CORPORATION), MultiFlex (Rigaku Corporation), and the like may be mentioned. Also, as the measurement apparatus for the optical system for parallel beam method, XRD-7700 (SHIMADZU CORPORATION), RINT2200Ultima+/PC (Rigaku Corporation), and the like may be mentioned.

When it is needed to measure the amount of the Compound 1 of the invention in a preparation, it is usually convenient and preferable to use HPLC. Specifically, for example, a calibration curve is prepared by performing measurement by HPLC, using a standard material of the Compound 1 of the invention with already known purity, and the amount of the Compound 1 of the invention in the sample can be quantified on the basis of this calibration curve.

The quantification method by means of HPLC and the method for measuring crystals with regard to the Compound 1 of the invention as described above are similarly applicable to the Compound 2 of the invention or the Compound 3 of the invention, that will be described later. For example, with regard to the HPLC conditions, it is possible to perform measurement under the same conditions as described above, and also for the measurement method by means of differential scanning calorimetric analysis, measurement can be made using characteristic endothermic peaks for the respective compounds. In addition, the respective crystal purity can also be calculated in the same manner as described above. Pure type A crystals and type B crystals of the Compound 1 of the invention to be used as the standard material in the measurement described above, as well as pure crystals of type A and type B of the Compound 1 of the invention to be used as the seed crystals used in the method for crystal production that will be described later, can be respectively obtained according to the respective methods described in Examples 3, 4 and 5, and then particularly selecting crystals of preferred shape among them, and further selecting the crystals which show a single characteristic endothermic peak by differential scanning calorimetric analysis. It is also possible to use the type B crystals obtained according to the respective methods of Examples 6 and 7, as the standard material. It is also possible to use the type B crystals obtained according to the respective methods of Examples 6 and 7 as the seed crystals for obtaining pure type B crystals. Incidentally, if type A crystals are contaminated by type B crystals, there are cases where the quantified value of the type A crystals obtained by differential scanning calorimetric analysis may be underestimated as compared to the quantified value of the type A crystals of authentic standard material. The extent of error in this case may vary depending on the rate of the contamination of type B crystals in the type A crystals, but for example, if the rate of the contamination of the type B crystals is within 10%, there is usually a possibility that an error of about 10% may be observed in the quantified value of the type A crystals. Also, if the rate of the contamination of the type B crystals is near 50%, there is a possibility for the occurrence of an error of up to about 20% at maximum. In contrast, if type B crystals are contaminated by type A crystals, there are cases where the quantified value of the type B crystals may be overestimated as compared to the quantified value of the type B crystals of authentic standard material. Although the extent of error in this case may also vary depending on the rate of the contamination of the type A crystals with respect to the type B crystals, for example, if the rate of the contamination of the type A crystals is within 10%, there is usually a possibility that an error of about 10% may be observed in the quantified value of the type B crystals. Also, if the rate of the contamination of the type A crystals is near 50%, there is a possibility for the occurrence of an error of up to about 20% at maximum. Particularly, even in the normal state where the rate of the contamination to each other is not so high, the crystal purity calculated for the type A crystals or of the type B crystals may include an error of about 10%. The quantification can therefore be conducted by preparing a calibration curve using a standard material having an expected rate of contamination.

Also, to determine the rate of contamination more precisely, a series of mixtures of the standard type A crystal and the standard type B crystal are prepared with predetermined ratios of mixing and a calibration curve is generated to show the relationship between the ratios (percentage) of the mixed crystals and the area of each endothermic peak (mJ) corresponding to the melting of each crystal as percentage based on the total peaks area. Then, the rate of the contamination in the sample product can be evaluated from this calibration curve.

With regard to the measurement methods other than differential scanning calorimetric analysis, namely, measurement methods such as powder X-ray diffraction spectrum, infrared absorption spectrum, solid $^{13}$C-NMR spectrum and Raman spectrum, it is also possible to determine the rate of the contamination more precisely from a calibration curve generated by using a series of mixtures of standard materials with predetermined ratios of mixing.

BEST MODE FOR CARRYING OUT THE INVENTION

Figure 1:
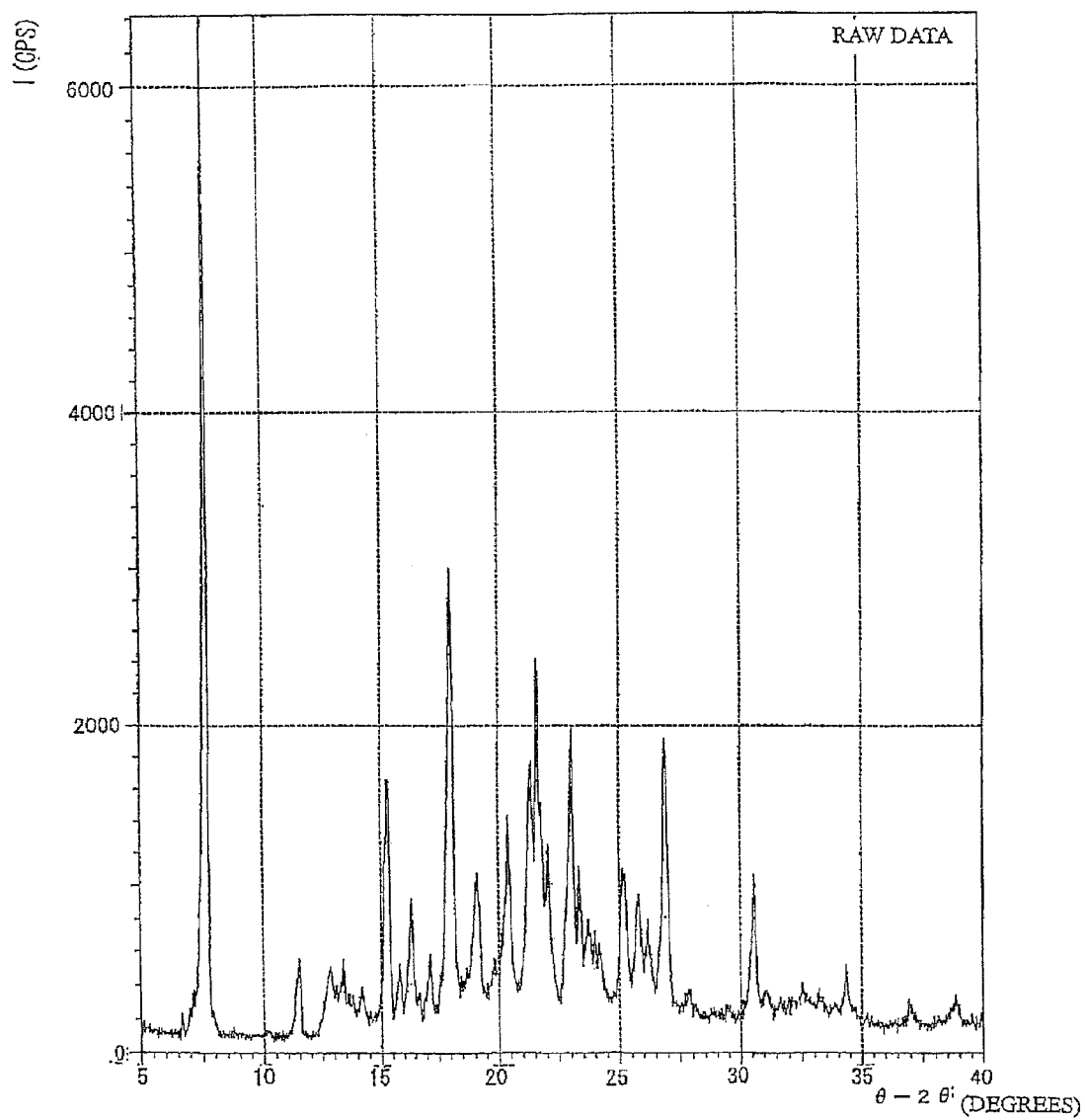
FIG. 1 is a powder X-ray diffraction spectrum of the crystals of Compound 2 of the invention. In the diagram, the vertical axis indicates intensity (CPS), and the horizontal axis indicates 2θ (°).

[Method for Producing Type A Crystals of Compound 1 of the Invention]

As the method of producing the type A crystals of the Compound 1 of the invention, there may be mentioned a method of adding an acid to a basic solution of the Compound 1 of the invention to produce crystals of the Compound 1 of the invention, and thus obtaining the crystals.

That is, the basic solution of the Compound 1 of the invention as used in the present invention is not particularly limited so long as it is a solution having the compound dissolved under basic conditions, and here, the compound to be dissolved may be in any of an oily state, solid state (including various crystal types and amorphous type), and mixtures thereof. The Compound 1 of the invention can be prepared according to the method described in International Patent Publication No. WO 03/70686.

Inorganic bases are preferred as the base used for preparing the basic solution as described above. That is, for example, alkali metal bases such as sodium hydroxide, potassium hydroxide, sodium carbonate, potassium carbonate, sodium methoxide and potassium t-butoxide, and the like may be mentioned. Sodium hydroxide, potassium hydroxide and the like are preferred, and sodium hydroxide may be mentioned as a particularly preferred example. These bases can be used in the form of a solution prepared by dissolving them in water or an alcohol such as methanol, ethanol or t-butanol. It is particularly preferable to prepare and use an aqueous solution containing a base at a predetermined concentration from the viewpoint that it is easy to define the amount of an acid to be added, and the like. However, in the case a concentrated basic solution is used, there is a concern that when an acid is added later, high heat due to the neutralization reaction would occur, and thus using a 0.5 to 2 N aqueous solution of base may be mentioned as a very preferable example.

The amount of base to be added may be, as the lower limit, usually 0.8 equivalents or more, preferably 0.9 equivalents or more, and more preferably 1.0 equivalent or more, relative to 1 equivalent of the compound. As the upper limit, usually 3.0 equivalents or less relative to 1 equivalent of the compound may be mentioned, and 2.0 equivalents or less may be mentioned as a preferred example.

As the solvent to be used for dissolving the compound together with the base, polar solvents may be preferably mentioned, and specifically, water, alcohols such as methanol and ethanol, ethers such as tetrahydrofuran and dioxane, acetone and the like may be mentioned. Mixtures thereof can also be used according to necessity. Among them, water, methanol, ethanol, tetrahydrofuran and the like are preferred, and water, methanol, ethanol and the like are particularly preferred. Furthermore, it is very preferable to use a mixture of water and methanol, and the ratio of mixing of water:methanol to be obtained after preparing a solution containing a base, may be, for example, 1:20 to 10:1, while a ratio of 1:10 to 1:1 is preferred.

The above-described basic solution may be heated at a temperature lower than or equal to the boiling point of the solvent, and if impurities are present, it is preferred to remove impurities by processes such as filtration.

As the acid to be added to the solution described above, the acid may be in any of liquid state, solid state and gaseous state, as long as the acid is not incorporated into the precipitate of crystals generated upon adding the acid. However, the acid is preferably in a solution state or gaseous state, while an acid in the solution state may be mentioned as a preferred example.

Furthermore, the type of acid may be any of organic acids and inorganic acids. However, since the acid to be used should neutralize the base, it is necessary that acidity of the acid be higher than the acidity of the compounds of the invention. Thus, mineral acids such as hydrochloric acid, sulfuric acid and phosphoric acid are preferred, and hydrochloric acid is particularly preferred. These can also be used in the form of a solution prepared by dissolving them in water or an alcohol such as methanol, ethanol or t-butanol. It is preferable to prepare and use an aqueous solution containing an acid at a predetermined concentration from the view point that it is easy to define the amount of the solution to be added, and the like. However, in the case a concentrated acidic solution is used, there is a concern that high heat due to the neutralization reaction would occur, and thus using a 0.5 to 2 N aqueous solution of acid may be mentioned as a particularly preferable example.

As the amount of acid to be added, the acid may be added to the extent that crystals are sufficiently generated, and therefore the amount is not particularly limited. However, for example, usually 0.8 equivalents or more, relative to 1 equivalent of base, may be mentioned, and it is preferable to add 0.9 equivalents or more. Also, it is particularly preferable to add about 1 equivalent. Furthermore, there is no particularly limitation concerning the upper limit, but for example, usually 1.5 equivalents or less, and preferably 1.2 equivalents or less relative to 1 equivalent of base may be mentioned.

The method of adding acid may be exemplified by (1) adding at once, (2) adding in several divided portions, (3) adding continuously over a period of time by adding dropwise, or the like, but a method of adding continuously over a period of time by a method such as dropwise addition is preferred. Upon adding an acid, it is preferable to perform stirring. The rate of addition may vary depending on the amount of the compound used, the concentration of the base in the basic solution, the type of the acid used, or the concentration of the acidic solution. However, in the case of using 0.5 to 2 N hydrochloric acid, there may be mentioned a method of adding the entire amount over 1 hour to 6 hours.

With regard to the temperature for the addition of acid, the upper limit is preferably 60° C. or lower, more preferably 50° C. or lower, and even more preferably 45° C. or lower, whereas the lower limit is preferably 0° C. or higher, more preferably 10° C. or higher, and even more preferably 25° C. or higher.

Obtaining the generated crystals may be performed usually within 24 hours, preferably within 20 hours, and particularly preferably within 10 hours, after the addition of acid. It is also possible to collect crystals immediately after the addition of acid, but it is preferable to collect the crystals after 1 hour of the addition of acid, and particularly preferably after 3 hours of the addition of acid.

As the method for collecting precipitated crystals, it is possible to obtain crystals by a known method such as filtration or decantation, but filtration is usually preferred. Furthermore, after collecting crystals by filtration, the crystals can be washed with a polar solvent, for example, water, methanol, ethanol or a mixture solution thereof, and this process is effective as a process for removing impurities. As the method of washing, a method of rinsing the crystals on the filtration vessel with a polar solvent is preferred. It is also preferable to use a method of introducing the crystals into a polar solvent such as water, methanol, ethanol or a mixture thereof to form a suspension, stirring the suspension sufficiently, and then filtering the crystals again to obtain the crystals. Furthermore, it is particularly preferable to perform both of the washing processes described above. The collected crystals can be dried by a generally performed drying method, such as drying under reduced pressure, drying under reduced pressure while heating, drying under normal pressure while heating, or air drying.

The final concentration of the compound after adding the acid to the basic solution to complete the precipitation may vary depending on the type of the solvent used, and in the case of a solvent mixture, it may also depends on the mixing ratio. However, the lower limit may be generally 1 w/v % or more, and preferably 5 w/v % or more. The upper limit may be preferably 30 w/v % or less, and more preferably 20 w/v % or less, for example.

Additionally, it is conceived that upon generating crystals, adding a small amount of type A crystals as seed crystals is a preferable embodiment.

As a preferred example among the methods for production described above, the following may be mentioned. In the following three examples of methods for production, the preferred examples described above can be employed for the amount of the base used, the stirring temperature before the addition of acid, the amount of the acid added, and the stirring time after the addition of acid.

A method of adding to a solution containing 3-[3-amino-4-(indan-2-yloxy)-5-(1-methyl-1H-indazol-5-yl)phenyl]propionic acid and 0.8 to 3.0 equivalents of sodium hydroxide or potassium hydroxide relative to the amount of said compound in water, methanol, ethanol, tetrahydrofuran or a solvent mixture thereof, 0.8 to 1.5 equivalents of an aqueous solution of hydrochloric acid, sulfuric acid or phosphoric acid relative to 1 equivalent of said base continuously over time by a method such as dropwise addition at a temperature of 10 to 50° C. with stirring; and further stirring for 1 to 24 hours to obtain crystals.

A method of adding to a solution containing the above compound and 0.9 to 2.0 equivalents of sodium hydroxide relative to 1 equivalent of said compound in water, methanol, ethanol or a solvent mixture thereof, 0.9 to 1.2 equivalents of a 0.5 to 2 N aqueous solution of hydrochloric acid relative to 1 equivalent of said base over 1 hour to 6 hours at a temperature of 25 to 45° C. with stirring; and further stirring for 3 to 24 hours to obtain crystals.

A method of adding to a solution of the above compound in a mixture of methanol and a 0.5 to 2 N aqueous solution of sodium hydroxide in an amount to give 0.9 to 2.0 equivalents of the base relative to 1 equivalent of said compound, a 0.5 to 2 N aqueous solution of hydrochloric acid in an amount corresponding to 0.9 to 1.2 equivalents relative to 1 equivalent of said base over 1 hour to 6 hours at a temperature of 25 to 45° C. with stirring; and further stirring for 3 to 24 hours to obtain crystals.

Furthermore, the basic solution of the Compound 1 of the invention may be an alkali hydrolysate of a lower alkyl ester of 3-[3-amino-4-(indan-2-yloxy)-5-(1-methyl-1H-indazol-5-yl)phenyl]propionic acid. That is, as another method of producing type A crystals, the following may be mentioned.

A method of subjecting a lower alkyl ester of 3-[3-amino-4-(indan-2-yloxy)-5-(1-methyl-1H-indazol-5-yl)phenyl]propionic acid to alkali hydrolysis in a solvent, and then adding an acid to said hydrolysate solution which is under basic conditions, to obtain crystals.

The "lower alkyl ester" includes a carboxylic acid ester of an alkyl group having 1 to 4 carbon atoms, and the alkyl group having 1 to 4 carbon atoms may be any of a methyl group, an ethyl group, an n-propyl group, an isopropyl group, an n-butyl group, an isobutyl group, a sec-butyl group and a t-butyl group. Among them, a methyl group and an ethyl group are particularly preferred examples.

The lower alkyl ester of 3-[3-amino-4-(indan-2-yloxy)-5-(1-methyl-1H-indazol-5-yl)phenyl]propionic acid can be prepared according to the method of International Patent Publication No. WO 03/70686.

As the base used in the preparation of the alkali hydrolysate of the compound described above, the bases used for making the above-described basic solution can be used.

The amount of the base used may be usually exemplified by 1 equivalent or more relative to 1 equivalent of the compound. As the upper limit, usually 10 equivalents or less may be mentioned relative to 1 equivalent of the compound, and preferably 3 equivalents or less, and particularly preferably 2 equivalents or less may be mentioned for example.

As the solvent, usually an inert solvent which does not interfere with the reaction, and preferably a solvent among polar solvents, which allows a reaction to occur, is preferred. Although reference can be made to the conditions described above, the polar solvent may be exemplified by water, methanol, ethanol, tetrahydrofuran, dioxane and the like may be mentioned, and if necessary, these can be mixed and used. Among these, water, methanol, ethanol, tetrahydrofuran and the like are preferred, and water, methanol, ethanol and the like are particularly preferred. Furthermore, it is very preferable to mix water and methanol for use, and after adding the base, the mixing ratio of water:methanol as the reaction solution may be 1:20 to 10:1, and a ratio of 1:10 to 1:1 is preferred.

In addition, for the reaction temperature of the alkali hydrolysate, an appropriate temperature may be selected, for example, from room temperature to the reflux temperature, and particularly preferably, for example, a condition of 50 to 70° C. may be mentioned. The reaction time may be exemplified by usually 0.5 to 72 hours, and preferably 1 to 24 hours. More specifically, as the upper limit, 24 hours or shorter is preferred, 20 hours or shorter is more preferred, and 10 hours or shorter is even more preferred. As the lower limit, 0.5 hours or longer is preferred, 1 hour or longer is more preferred, and 3 hours or longer is even more preferred. However, since it is possible to trace the progress of reaction by thin layer chromatography (TLC), high performance liquid chromatography (HPLC) or the like, usually the reaction may be appropriately terminated when the obtainable yield of 3-[3-amino-4-(indan-2-yloxy)-5-(1-methyl-1H-indazol-5-yl)phenyl]propionic acid reaches the maximum.

After the alkali hydrolysis reaction, the acid to be added to the solution which is under basic conditions, the conditions for generating crystals, the method of collecting, and the like are as described above.

Among the production method described above, a preferred example may be the following. For the following three examples of the production method, with regard to the amount of the base used for the alkali hydrolysis, the reaction temperature of the hydrolysis reaction, the reaction time of the hydrolysis reaction, the stirring temperature before the addition of acid, the amount of acid to be added, and the stirring time after the addition of acid, the preferred examples described above can be employed.

A method of allowing a lower alkyl ester of 3-[3-amino-4-(indan-2-yloxy)-5-(1-methyl-1H-indazol-5-yl)phenyl]propionic acid to react in water, methanol, ethanol, tetrahydrofuran or a solvent mixture thereof in the presence of 1 to 3 equivalents of sodium hydroxide or potassium hydroxide relative to 1 equivalent of the lower alkyl ester at 50 to 70° C. for 1 to 24 hours; then adding at a temperature of 10 to 50° C. with stirring, 0.8 to 1.5 equivalents of an aqueous solution of hydrochloric acid, sulfuric acid or phosphoric acid relative to 1 equivalent of the base continuously over time by a method such as dropwise addition; and then stirring for 1 to 24 hours to obtain the crystals.

A method of allowing a methyl or ethyl ester of 3-[3-amino-4-(indan-2-yloxy)-5-(1-methyl-1H-indazol-5-yl)phenyl]propionic acid to react in water, methanol, ethanol or a solvent mixture thereof in the presence of 1 to 2 equivalents of sodium hydroxide relative to 1 equivalent of the methyl or ethyl ester at 50 to 70° C. for 1 to 24 hours; then adding at a temperature of 25 to 45° C. with stirring, 0.9 to 1.2 equivalents of a 0.5 to 2 N aqueous solution of hydrochloric acid relative to the base over 1 hour to 6 hours; and then stirring for 3 to 24 hours to obtain the crystals.

A method of adding to a methyl or ethyl ester of 3-[3-amino-4-(indan-2-yloxy)-5-(1-methyl-1H-indazol-5-yl)phenyl]propionic acid, a mixture of methanol and 1 to 2 equivalents of a 0.5 to 2 N aqueous solution of sodium hydroxide relative to 1 equivalent of the methyl or ethyl ester, allowing the mixture to react at 50 to 70° C. for 1 to 24 hours; then adding, at a temperature of 25 to 45° C. with stirring, 0.9 to 1.2 equivalents of a 0.5 to 2 N aqueous solution of hydrochloric acid relative to 1 equivalent of the base, over 1 hour to 6 hours; and then stirring for 3 to 24 hours to obtain the crystals.

[Method for Producing Type B Crystals of Compound 1 of Invention]

As the method of producing type B crystals of the Compound of the invention, there may be mentioned a method of crystallizing the Compound 1 of the invention from a solution having the compound dissolved in any one or two or more solvents selected from the group consisting of acetone, dichloromethane, methanol, ethyl acetate, a methanol/acetic acid mixture solution, and acetonitrile.

The Compound 1 of the invention can be prepared according to the method described in International Patent Publication No. WO 03/70686 or the like, as described above.

Furthermore, as the solvent to be used for the above, acetone, dichloromethane, methanol, ethyl acetate, acetonitrile, tetrahydrofuran, diisopropyl ether, nitrobenzene, 2,2,2-trifluoroethanol, N,N-dimethylformamide, N,N-dimethylacetamide and the like may be mentioned, and these solvents can also be mixed and used. Furthermore, tetrahydrofuran/water, N,N-dimethylformamide/water, N,N-dimethylacetamide/water, tetrahydrofuran/methanol, diisopropyl ether/acetic acid, methanol/acetic acid, and the like may be mentioned. Among these, acetone, dichloromethane, methanol, ethyl acetate, acetonitrile, methanol/acetic acid and the like are preferred, and acetone, dichloromethane and the like are particularly preferred.

Upon dissolving the compound in a solvent, it is preferable to heat the solution to a temperature lower than or equal to the boiling point of the solvent, from the view point of the obtainable yield of the resulting crystals, and the like, and if impurities are present, the impurities may be removed by processes such as filtration.

The amount of the solvent to be added may vary depending on the type of the solvent used, and in the case of a solvent mixture, on the mixing ratio. However, it is preferable to use the solvent in an amount which dissolves the compound at a temperature equal to or below the boiling point of the solvent used, and it is particularly preferable to use an amount which dissolves the compound around the boiling point of the solvent to the saturated concentration, from the viewpoint of the obtainable yield of the resulting crystals. Specifically, for example, in the case of using acetone as the solvent, 15 to 25 ml based on 1 g of the compound is preferable, and about 15 ml may be mentioned as a more preferred example. Also, in the case of using dichloromethane, for example, it is preferable to use an amount of 30 to 50 ml based on 1 g of the compound, and about 30 ml may be mentioned as more preferred example.

As the method of cooling the solution of compound prepared with heating, there may be mentioned methods such as rapid cooling, gradually cooling, allowing the solution to naturally cool itself, and the like. However, a method of gradually cooling or a method of allowing the solution to naturally cool itself is preferred.

The degree of cooling may vary depending on the amount of the solvent used, the type of the solvent used, and in the case of a solvent mixture, on the mixing ratio, and may vary depending on the temperature during the process of dissolving the compound. However, it is preferable to cool the solution below a temperature at which the saturated concentration of the compound is reached.

The cooling step may be performed while stirring, or may be performed while standing still. However, it is preferable to perform cooling while stirring from the viewpoint of accelerating precipitation of crystals and shortening the operation time.

Additionally, upon generating crystals by the method described above, adding a small amount of type B crystals as seed crystals is also a preferred aspect.

Collection of precipitated crystals can be generally performed by filtration. Further, after collecting the crystals by filtration, the crystals can be washed with a solvent used in dissolving the compound or a solvent which does not significantly dissolve the crystals, or a mixture solution thereof. This step is effective for removing impurities.

The collected crystals can be dried by a generally performed drying method, such as drying under reduced pressure, drying under reduced pressure while heating, drying under normal pressure while heating, or air drying.

A preferred example of the above production method may be exemplified by the following.

A method of adding a 15 to 25 ml portion of acetone or a 30 to 50 ml portion of dichloromethane to 1 g of the Compound 1 of the Invention, heating the mixture to a temperature near the boiling point of the solvent to dissolve the compound, filtering impurities as necessary; subsequently stirring at room temperature for several hours to several days; and then obtaining the generated crystals.

As another production method regarding the type B crystals of the Compound 1 of the invention, there may be mentioned a method of adding type B crystals of Compound 1 of the invention as seed crystals during the process of adding an acid to a basic solution of the Compound 1 of the invention but immediately before the Compound 1 of the invention starts to crystallize, thereby allowing the Compound 1 of the invention to crystallize as the type B crystal, and obtaining the crystals.

The Compound 1 of the invention used in the present invention, its form, and the method of obtaining the compound are the same as those described in the description in the section "Method for producing type A crystals of Compound 1 of the invention." Furthermore, the same method as described in the above can be used for preparing a basic solution of the Compound 1 of the invention. Also, it is the same as described above that the basic solution may be an alkali hydrolysate of a lower alkyl ester of 3-[3-amino-4-(indan-2-yloxy)-5-(1-methyl-1H-indazol-5-yl)phenyl]propionic acid.

Moreover, the same as those described in the above may equally apply to the type, amount of addition or the like of the base used for preparing the basic solution; the type, amount of addition or the like of the solvent used for dissolving the compound together with the base; and the type or amount of addition of the acid to be added, the method of addition, rate of addition, temperature during addition, and the like. For the method for adding seed crystals of the type B crystals, it is preferable that no crystal is present in the mixture solution when the seed crystals are added, and it is preferable that the added seed crystals are not dissolved in the solution. In the case of adding an acid to the solution of the compound prepared by adding thereto a base in an amount equal to or excessive over the amount of the compound, it is preferable to add the seed crystals of the type B crystals when the excessive base is neutralized by the added acid from the viewpoint of avoiding dissolution of the seed crystals. Furthermore, at that time, it is also a preferable method to confirm the neutralization of the excessive base, using an instrument such as a pH meter. That is, for example, if the compound has been dissolved by using 1.5 equivalents of the base relative to the compound, the seed crystals may be introduced after the pH of the solution shows weak basicity e.g. about pH 7 to 9 by the addition of an acid in an amount equivalent to 0.5 equivalents, may be mentioned as a preferable example. Also, it is preferable to add the seed crystals before crystals are generated upon the addition of acid. When 2 N hydrochloric acid is added over 1 hour to 6 hours, since it is highly probable that the crystallization takes place when the pH of the solution shows weak acidity as the excessive base is neutralized and 0.1 to 0.2 equivalents of an acid is further added, it is preferable to add the seed crystal of the type B crystals even at an earlier stage than that.

The amount of the type B crystals to be added as the seed is not particularly limited as long as the added crystals do not dissolve. However, the amount may be usually 0.01% or more based on the dissolved compound, and for example, addition of preferably 0.0.5% or more, and particularly preferably about 0.1%, may be mentioned. Although the upper limit is not particularly limited, for example, usually 2% or less based on the compound may be mentioned, and preferably 1.5% or less, more preferably 1.0% or less, and particularly preferably 0.3% or less, may be exemplified. With regard to the method of collecting the precipitated crystals, the method of drying the collected crystals, the final concentration of the compound after the addition of acid, and the like, conditions that are the same as those described in the section "Method for producing type A crystals of Compound 1 of the invention" described above can be used.

As preferred examples among the above-described methods for production, the following may be exemplified. For the following three examples of the production method, the preferred examples described above can be employed with regard to the amount of base used, the stirring temperature before the addition of acid, the amount of acid to be added, the amount of the type B seed crystals to be added, and the stirring time after the addition of acid.

A method of adding, at a temperature of 10 to 50° C. with stirring, to a solution of the Compound 1 of the invention in water, methanol, ethanol, tetrahydrofuran or a solvent mixture thereof containing 0.8 to 3.0 equivalents of sodium hydroxide or potassium hydroxide relative to 1 equivalent of said compound, an aqueous solution of 0.8 to 1.5 equivalents of hydrochloric acid, sulfuric acid or phosphoric acid relative to 1 equivalent of the base continuously over time by a method such as dropwise addition; and in the middle of the addition of the acid and when the pH of the solution shows weak basicity of pH 7 to 9, adding thereto the type B seed crystals in an amount of 0.01 to 2% relative to said compound; and then stirring for 1 to 24 hours to obtain the crystals.

A method of adding, at a temperature of 25 to 45° C. with stirring, to a solution of the Compound 1 of the invention in water, methanol, ethanol or a solvent mixture thereof containing 0.9 to 2.0 equivalents of sodium hydroxide relative to 1 equivalent of said compound, 0.9 to 1.2 equivalents of a 0.5 to 2 N aqueous solution of hydrochloric acid relative to 1 equivalent of the base over 1 hour to 6 hours; and in the middle of the addition of the acid and when the pH of the solution shows weak basicity of pH 7 to 9, adding thereto the type B seed crystals in an amount of 0.05 to 1.5% relative to said compound; and then stirring for 1 to 5 hours to obtain the crystals.

A method of adding, at a temperature of 25 to 45° C. with stirring, to a solution of the Compound 1 of the invention in a mixture of methanol and 0.9 to 2.0 equivalents of a 0.5 to 2 N aqueous solution of sodium hydroxide relative to 1 equivalent of said compound, 0.9 to 1.2 equivalents of a 0.5 to 2 N aqueous solution of hydrochloric acid relative to 1 equivalent of the base over 1 hour to 6 hours; and in the middle of the addition of the acid and when the pH of the solution shows weak basicity of pH 7 to 9, adding thereto the type B seed crystals in an amount of 0.1% relative to the compound; and then stirring for 1 to 5 hours to obtain the crystals.

Furthermore, as preferred examples of the production method, the following embodiments may be mentioned. For the following three examples of the production method, the above-described preferred examples can be employed with regard to the amount of the base used in the alkali hydrolysis, the reaction temperature of the hydrolysis reaction, the reaction time of the hydrolysis reaction, the stirring temperature before the addition of acid, the amount of acid to be added, the amount of type B seed crystals to be added, and the stirring time after the addition of acid.

A method of allowing a lower alkyl ester of 3-[3-amino-4-(indan-2-yloxy)-5-(1-methyl-1H-indazol-5-yl)phenyl]propionic acid to react in water, methanol, ethanol, tetrahydrofuran or a solvent mixture thereof in the presence of 1 to 3 equivalents of sodium hydroxide or potassium hydroxide relative to 1 equivalent of the lower alkyl ester at 50 to 70° C. for 1 to 24 hours; subsequently adding, at a temperature of 10 to 50° C. with stirring, 0.8 to 1.5 equivalents of an aqueous solution of hydrochloric acid, sulfuric acid or phosphoric acid relative to 1 equivalent of the base continuously over time by a method such as dropwise addition; and in the middle of the addition of the acid and when the pH of the solution shows weak basicity of pH 7 to 9, adding thereto the type B seed crystals in an amount of 0.01 to 2% relative to the compound; and then stirring for 1 to 24 hours to obtain the crystals.

A method of allowing a methyl or ethyl ester of 3-[3-amino-4-(indan-2-yloxy)-5-(1-methyl-1H-indazol-5-yl)phenyl]propionic acid to react in water, methanol, ethanol or a solvent mixture thereof in the presence of 1 to 2 equivalents of sodium hydroxide relative to 1 equivalent of the methyl or ethyl ester at 50 to 70° C. for 1 to 24 hours, subsequently adding, at a temperature of 25 to 45° C. with stirring, 0.9 to 1.2 equivalents of a 0.5 to 2 N aqueous solution of hydrochloric acid relative to the base over 1 hour to 6 hours; and in the middle of the addition of the acid and when the pH of the solution shows weak basicity of pH 7 to 9, adding thereto the type B seed crystals in an amount of 0.05 to 1.5% relative to the compound; and then stirring for 3 to 24 hours to obtain the crystals.

A method of adding to a methyl or ethyl ester of 3-[3-amino-4-(indan-2-yloxy)-5-(1-methyl-1H-indazol-5-yl)phenyl]propionic acid, a mixture of methanol and 1 to 2 equivalents of a 0.5 to 2 N aqueous solution of sodium hydroxide relative to 1 equivalent of the methyl or ethyl ester, allowing the mixture to react at 50 to 70° C. for 1 to 24 hours, subsequently adding, at a temperature of 25 to 45° C. with stirring, 0.9 to 1.2 equivalents of a 0.5 to 2 N aqueous solution of hydrochloric acid relative to 1 equivalent of the base over 1 hour to 6 hours; and in the middle of the addition of the acid and when the pH of the solution shows weak basicity of pH 7 to 9, adding thereto the type B seed crystals in an amount of 0.1% relative to the compound; and then stirring for 3 to 24 hours to obtain the crystals.

[Method for Producing Crystals of Compound 2 of the Invention]

Furthermore, the crystal of Compound 2 of the invention is highly advantageous in the formulation processes, from the viewpoints that it is easy to make the content of the compound of the invention constant in each preparation, and the like. Further, the crystal is also favorable from the viewpoint that it is easy to remove solvents and the like therefrom, compared to the case of oily matter, and discovery of the method of producing the crystals advantageously allows the compound of the invention to be obtained with good purity, without performing the purification by column chromatography which is needed in the above-described known methods for production. Thus, the method is suitable for the production in an industrial scale, which is extremely desirable.

As the method of producing the crystals of Compound 2 of the invention, there may be mentioned a method of adding to a solution prepared by dissolving the Compound 2 of the invention in a good solvent which easily dissolves the compound, a poor solvent in which the compound does not dissolve well, thereby to generate crystals of the compound, and obtaining the crystals. In the above, the Compound 2 of the invention can be prepared according to the method described in International Patent Publication No. WO 03/70686.

As the good solvent that is used for dissolving the compound, toluene, ethyl acetate, tetrahydrofuran, acetone, dimethoxyethane, methanol and the like may be mentioned, and acetone, toluene, tetrahydrofuran and the like are preferred, with acetone being particularly preferred. Furthermore, as the poor solvent that is added to generate crystals of the compound, heptane, diisopropyl ether, isopropanol, t-butyl methyl ether, water and the like may be mentioned. However, in the case of using acetone as the good solvent, water is preferred, and in the case of using toluene or tetrahydrofuran as the good solvent, heptane is preferred. A combination of using acetone as the good solvent and water as the poor solvent may be mentioned as a particularly preferable example.

For the concentration of the solution prepared with the good solvent, the upper limit is preferably 20 w/v % or less, and more preferably 10 w/v % or less, while the lower limit is preferably 5 w/v % or more. For the amount of the poor solvent to be added, the upper limit is preferably 2.0 times or less, preferably 1.5 times or less, and more preferably 1.1 times or less than the amount of the good solvent, whereas the lower limit is preferably 0.8 times or more, and more preferably 0.9 times or more than the amount of the good solvent. In particular, it is preferable to add an amount of 1.0-fold. Furthermore, adding an amount of 1.05-fold is another particularly preferred aspect. As the method of adding the poor solvent, a method of adding continuously over time by a method such as dropwise addition is preferred. When adding a poor solvent, it is preferable to perform stirring. The rate of addition may vary depending on the amount of the compound used, the concentration of the compound in the solution, the good solvent used, and the type of the poor solvent, but in the case of adding water as the poor solvent to an acetone solution of the compound, a method of adding over 1 hour to 3 hours may be mentioned as an example.

For the temperature during the addition of the poor solvent, the upper limit is preferably 50° C. or less, more preferably 40° C. or less, and even more preferably 30° C. or less, whereas the lower limit is preferably 0° C. or higher, more preferably 10° C. or higher, and even more preferably 20° C. or higher.

The generated crystals may be collected, for example, usually after 1 hour to 24 hours of the addition of poor solvent, and preferably after 1 hour to 5 hours of the addition.

As the method of collecting the precipitated crystals, crystals can be obtained by known methods such as filtration and decantation, but usually filtration is preferred. Also, after collecting the crystals by filtration, the crystals can be washed with a polar solvent such as water, acetone or a mixture solution thereof, and this process is effective for removing impurities.

The collected crystals can be dried by a generally performed drying method, such as drying under reduced pressure, drying under reduced pressure while heating, drying under normal pressure while heating, or air drying.

[Method for Producing Crystals of Compound 3 of the Invention]

In addition, the crystal of Compound 3 of the present invention is highly advantageous in the formulation processes from the viewpoints that it is easy to make the content of the compound of the invention constant in each preparation, and the like. Further, the crystal is also favorable from the viewpoint that it is easy to remove solvents and the like therefrom, compared to the case of oily matter, and discovery of the method of producing the crystals advantageously allows the compound of the invention to be obtained with good purity, without performing the purification by column chromatography which is needed in the above-described known methods for production. Thus, the method is suitable for the production in an industrial scale, which is extremely preferred.

As the method of producing the crystals of Compound 3 of the invention, there may be mentioned a method of adding to a solution prepared by dissolving the Compound 3 of the invention in a good solvent which easily dissolves the compound, a poor solvent in which the compound does not dissolve well, thereby to generate crystals of the compound, and obtaining the crystals.

In the above, the Compound 3 of the invention can be prepared according to the method described in International Patent Publication No. WO 03/70686. Also, the compound can be produced using a conventional methyl-esterification reaction, for example, by methyl-esterifying 3-[3-amino-4-(indan-2-yloxy)-5-(1-methyl-1H-indazol-5-yl)phenyl]propionic acid in a methanol solvent under acidic conditions, or the like.

As the good solvent that is used for dissolving the compound, toluene, ethyl acetate, tetrahydrofuran, acetone and the like may be mentioned, and acetone, tetrahydrofuran and the like are preferred, with tetrahydrofuran being particularly preferred. Furthermore, as the poor solvent, heptane, isopropanol, methanol, water and the like may be mentioned. However, in the case of using acetone as the good solvent, water or heptane is preferred, and in the case of using tetrahydrofuran as the good solvent, heptane, isopropanol or water is preferred. A combination of using tetrahydrofuran as the good solvent and water as the poor solvent may be mentioned as a particularly preferable example.

For the concentration of the solution prepared with the good solvent, the upper limit is preferably 20 w/v % or less, and more preferably 10 w/v % or less, while the lower limit is preferably 5 w/v % or more. For the amount of the poor solvent to be added, the upper limit is preferably 2.0 times or less, preferably 1.5 times or less, and more preferably 1.1 times or less than the amount of the good solvent, whereas the lower limit is preferably 0.8 times or more, and more preferably 0.9 times or more than the amount of the good solvent. In particular, it is preferable to add an amount of 1.0-fold. Furthermore, adding an amount of 1.05-fold is another particularly preferred aspect. As the method of adding the poor solvent, a method of adding continuously over time by a method such as dropwise addition is preferred. When adding a poor solvent, it is preferable to perform stirring. The rate of addition may vary depending on the amount of the compound used, the concentration of the compound in the solution, the good solvent used, and the type of the poor solvent, but in the case of adding water as the poor solvent to a tetrahydrofuran solution of the compound, a method of adding over 1 hour to 3 hours may be mentioned as an example.

For the temperature during the addition of the poor solvent, the upper limit is preferably 50° C. or less, more preferably 40° C. or less, and even more preferably 35° C. or less, whereas the lower limit is preferably 0° C. or higher, more preferably 10° C. or higher, and even more preferably 25° C. or higher.

The generated crystals may be collected, for example, usually after 1 hour to 24 hours of the addition of poor solvent, and preferably after 1 hour to 5 hours of the addition.

As the method of collecting the precipitated crystals, crystals can be obtained by known methods such as filtration and decantation, but usually filtration is preferred. Also, after collecting the crystals by filtration, the crystals can be washed with a polar solvent such as water, acetone or a mixture solution thereof, and this process is effective for removing impurities.

The collected crystals can be dried by a generally performed drying method, such as drying under reduced pressure, drying under reduced pressure while heating, drying under normal pressure while heating, or air drying.

The compounds of the invention suppress inflammatory edema in mouse, allergic edema, acetic acid writhing reaction, and rat adjuvant arthritis by oral administration at a dose of 0.1 to 500 mg/kg, while causing no death among mice by oral administration at a dose of 500 mg/kg/day for 3 days. Thus, the compounds are safe compounds as drugs for mammals, preferably humans, pets or companion animals such as dogs and cats, and farm animals, and they are useful substances as active ingredients of pharmaceutical products. As the medicaments for mammals, preferably humans, pets or companion animals such as dogs and cats, or farm animals, there may be mentioned, as preferred examples, any of the prophylactic and/or therapeutic agent for conditions, various diseases, and pathological conditions in which various acute or chronic inflammatory reactions resulting from production of prostaglandin and/or leukotriene are recognized, and specifically inflammatory diseases, allergic diseases, autoimmune diseases, and pain.

In order to use the compounds of the invention as the medicaments described above, an effective amount of the compounds of the invention may be directly used, or may be mixed with a pharmaceutically acceptable carrier to form a pharmaceutical composition. This carrier may be exemplified by a suspending agent such as carboxymethylcellulose, or other known carriers can also be used. For example, there may be mentioned a method of suspending the compounds of the present invention in purified water containing 0.5% carboxymethylcellulose.

Examples of the dosage form for formulating the above-mentioned pharmaceutical composition include tablet, powder, granule, syrup, suspension, capsule, injection and the like. Considering the nature of the crystals of the compounds of the invention, it is particularly preferable that the pharmaceutical composition is a dry preparation. For the manufacture of such preparations, various carriers are used in accordance with these preparations. For example, as the carrier for oral preparations, there can be mentioned excipients, binders, lubricants, flowability promoters, and colorants.

When the compounds of the present invention are formulated as a parenteral preparation such as an injection, generally distilled water for injection, physiological saline, aqueous glucose solution, plant oils for injection, propylene glycol, polyethylene glycol and the like can be used as a diluent. According to necessity, disinfectants, antiseptics, stabilizers, isotonic agents, soothing agents and the like may also be added.

In the case of administering the compounds of the present invention to mammals, for example, humans, the compounds can be orally administered in the form of tablets, powders, granules, suspensions, capsules or the like, and can also be parenterally administered in the form of injection including a drip infusion, a suppository, a gel, a lotion, an ointment, a cream, or a spray. The dose may vary depending on the disease to be applied, administration route, the age, weight and severity of symptoms of the patient, and the like, but in general an exemplary dose for an adult may be 1 to 1000 mg per day, which is administered in 1 to 3 divided portions. The administration period is generally an everyday administration for several days to two months. However, depending on the patient's symptoms, both the daily dose and the administration period may be increased or decreased.

As analogous compounds of the compounds of the invention, the following compounds may be mentioned, and these compounds can also be prepared according to the method described in International Patent Publication No. WO 03/70686, or by the methods described in the present specification.

3-[3-Amino-4-(indan-2-yloxy)-5-(1H-indazol-5-yl)phenyl]propionic acid;
3-[3-Amino-5-(1-ethyl-1H-indazol-5-yl)-4-(indan-2-yloxy)phenyl]propionic acid;
3-[4-(Indan-2-yloxy)-3-(N-methylamino)-5-(1-methyl-1H-indazol-5-yl)phenyl]propionic acid;
3-[4-(Indan-2-yloxy)-5-(1H-indazol-5-yl)-3-(N-methylamino)phenyl]propionic acid;
3-[5-(1-Ethyl-1H-indazol-5-yl)-4-(indan-2-yloxy)-3-(N-methylamino)phenyl]propionic acid;
3-[3-Amino-4-(4-fluoroindan-2-yloxy)-5-(1-methyl-1H-indazol-5-yl)phenyl]propionic acid and isomers thereof;
3-[3-Amino-4-(5-fluoroindan-2-yloxy)-5-(1-methyl-1H-indazol-5-yl)phenyl]propionic acid and isomers thereof;
3-[3-Amino-4-(5,6-difluoroindan-2-yloxy)-5-(1-methyl-1H-indazol-5-yl)phenyl]propionic acid;
3-[3-Amino-4-hydroxyindan-2-yloxy)-5-(1-methyl-1H-indazol-5-yl)phenyl]propionic acid and isomers thereof;
3-[3-Amino-4-(4-hydroxyindan-2-yloxy)-5-(1-methyl-1H-indazol-5-yl)phenyl]propionic acid and isomers thereof;
3-[3-Amino-4-(5-hydroxyindan-2-yloxy)-5-(1-methyl-1H-indazol-5-yl)phenyl]propionic acid and isomers thereof;
3-[3-Amino-4-(5,6-dihydroxyindan-2-yloxy)-5-(1-methyl-1H-indazol-5-yl)phenyl]propionic acid;
3-[3-Amino-4-(4-methoxyindan-2-yloxy)-5-(1-methyl-1H-indazol-5-yl)phenyl]propionic acid and isomers thereof;
3-[3-Amino-4-(5-methoxyindan-2-yloxy)-5-(1-methyl-1H-indazol-5-yl)phenyl]propionic acid and isomers thereof;
3-[3-Amino-4-(5,6-dimethoxyindan-2-yloxy)-5-(1-methyl-1H-indazol-5-yl)phenyl]propionic acid;
3-[3-Amino-4-(4-benzyloxyindan-2-yloxy)-5-(1-methyl-1H-indazol-5-yl)phenyl]propionic acid and isomers thereof;
3-[3-Amino-4-(4-benzyloxyindan-2-yloxy)-5-(1-methyl-1H-indazol-5-yl)phenyl]propionic acid and isomers thereof;
3-[3-Amino-4-(5,6-dibenzyloxyindan-2-yloxy)-5-(1-methyl-1H-indazol-5-yl)phenyl]propionic acid;
3-[3-Amino-4-(4-fluoroindan-2-yloxy)-5-(1H-indazol-5-yl)phenyl]propionic acid and isomers thereof;
3-[3-Amino-4-(5-fluoroindan-2-yloxy)-5-(1H-indazol-5-yl)phenyl]propionic acid and isomers thereof;
3-[3-Amino-4-(5,6-difluoroindan-2-yloxy)-5-(1H-indazol-5-yl)phenyl]propionic acid;
3-[3-Amino-4-(1-hydroxyindan-2-yloxy)-5-(1H-indazol-5-yl)phenyl]propionic acid and isomers thereof;
3-[3-Amino-4-(4-hydroxyindan-2-yloxy)-5-(1H-indazol-5-yl)phenyl]propionic acid and isomers thereof;
3-[3-Amino-4-(5-hydroxyindan-2-yloxy)-5-(1H-indazol-5-yl)phenyl]propionic acid and isomers thereof;
3-[3-Amino-4-(5,6-dihydroxyindan-2-yloxy)-5-(1H-indazol-5-yl)phenyl]propionic acid;
3-[3-Amino-5-(1H-indazol-5-yl)-4-(4-methoxyindan-2-yloxy)phenyl]propionic acid and isomers thereof;
3-[3-Amino-5-(1H-indazol-5-yl)-4-(5-methoxyindan-2-yloxy)phenyl]propionic acid and isomers thereof;
3-[3-Amino-4-(5,6-dimethoxyindan-2-yloxy)-5-(indazol-5-yl)phenyl]propionic acid;
3-[3-Amino-4-(4-benzyloxyindan-2-yloxy)-5-(1H-indazol-5-yl)phenyl]propionic acid and isomers thereof;
3-[3-Amino-4-(4-benzyloxyindan-2-yloxy)-5-(1H-indazol-5-yl)phenyl]propionic acid and isomers thereof;
3-[3-Amino-4-(5,6-dibenzyloxyindan-2-yloxy)-5-(1H-indazol-5-yl)phenyl]propionic acid;
3-[3-Amino-5-(1-ethyl-1H-indazol-5-yl)-4-(4-fluoroindan-2-yloxy)phenyl]propionic acid and isomers thereof;
3-[3-Amino-5-(1-ethyl-1H-indazol-5-yl)-4-(5-fluoroindan-2-yloxy)phenyl]propionic acid and isomers thereof;
3-[3-Amino-4-(5,6-difluoroindan-2-yloxy)-5-(1-ethyl-1H-indazol-5-yl)phenyl]propionic acid;
3-[3-Amino-5-(1-ethyl-1H-indazol-5-yl)-4-(1-hydroxyindan-2-yloxy)phenyl]propionic acid and isomers thereof;
3-[3-Amino-5-(1-ethyl-1H-indazol-5-yl)-4-(4-hydroxyindan-2-yloxy)phenyl]propionic acid and isomers thereof;
3-[3-Amino-5-(1-ethyl-1H-indazol-5-yl)-4-(5-hydroxyindan-2-yloxy)phenyl]propionic acid and isomers thereof;
3-[3-Amino-4-(5,6-dihydroxyindan-2-yloxy)-5-(1-ethyl-1H-indazol-5-yl)phenyl]propionic acid;
3-[3-Amino-5-(1-ethyl-1H-indazol-5-yl)-4-(4-methoxyindan-2-yloxy)phenyl]propionic acid and isomers thereof;
3-[3-Amino-5-(1-ethyl-1H-indazol-5-yl)-4-(5-methoxyindan-2-yloxy)phenyl]propionic acid and isomers thereof;
3-[3-Amino-4-(5,6-dimethoxyindan-2-yloxy)-5-(1-ethyl-1H-indazol-5-yl)phenyl]propionic acid;
3-[3-Amino-4-(4-benzyloxyindan-2-yloxy)-5-(1-ethyl-1H-indazol-5-yl)phenyl]propionic acid and isomers thereof;
3-[3-Amino-4-(4-benzyloxyindan-2-yloxy)-5-(1-ethyl-1H-indazol-5-yl)phenyl]propionic acid and isomers thereof; and 3-[3-Amino-4-(5,6-dibenzyloxyindan-2-yloxy)-5-(1-ethyl-1H-indazol-5-yl)phenyl]propionic acid.

EXAMPLES

Hereinafter, the present invention will be described in more detail by way of Examples and Test Examples, but the present invention is not intended to be limited thereto.

Example 1

Preparation Example 1 for Crystals of methyl 3-[4-(indan-2-yloxy)-3-(1-methyl-1H-indazol-5-yl)-5-nitrophenyl]propionate (Compound 2 of the Invention)

THF (40 ml) was added to methyl 3-[3-bromo-4-(indan-2-yloxy)-5-nitrophenyl]propionate (14.00 g, prepared according to the method of International Patent Publication No. WO 03/70686), 1-methyl-1H-indazol-5-boronic acid (7.62 g, prepared according to the method of International Patent Publication No. WO 03/70686), palladium acetate (75 mg, Wako Pure Chemical Industries, Ltd.) and triphenylphosphine (0.17 g, Wako Pure Chemical Industries, Ltd.), and the mixture solution was stirred. Then, a solution having tripotassium phosphate (16.97 g, Wako Pure Chemical Industries, Ltd.) dissolved in water (27 ml) was added to the above mixture, and the mixture solution was purged with nitrogen. Then, this mixture solution was stirred for 4 hours at 60° C. to react. After confirming the completion of the reaction, the reaction solution was partitioned to obtain the upper layer. The upper layer was cooled to room temperature, ethyl acetate (40 ml) and activated carbon (2.8 g, Japan Envirochemicals, Ltd.) were added thereto, and the mixture solution was further stirred for 1 hour at room temperature. The suspension was filtered to obtain a filtrate, and the residue was washed on the filter with ethyl acetate (20 ml) to obtain the wash solution. The filtrate and the wash solution were combined and concentrated under reduced pressure to obtain a concentrate (44 g). Then, acetone (140 ml) was added to the concentrate. The mixture solution was stirred and water (140 ml) was added thereto over 1 hour while stirring. The mixture solution was further stirred for another 1 hour at room temperature. Then, this mixture solution was filtered, the solids were washed on the filter with water (70 ml), and wet solids were obtained. These wet solids were dried under reduced pressure at 50° C. to obtain crystals of the title compound (15.7 g).

Example 1-A, B

Preparation Example 2 for Crystals of Compound 2 of the Invention

Crystals of the compound can be obtained by according to the processes of Example 1 except for adding toluene instead of acetone to the concentrate, and adding heptane instead of water.

Crystals of Compound 2 of the invention can also be obtained by adding tetrahydrofuran instead of acetone, and using heptane instead of water as used in Example 1.

Example 2

Preparation Example 1 of methyl 3-[3-amino-4-(indan-2-yloxy)-5-(1-methyl-1H-indazol-5-yl)phenyl]propionate (Compound 3 of the Invention)

To the Compound 2 of the invention (13.0 g) prepared according to Example 1, THF (138 ml), stabilized nickel (4.42 g, NIKKI CHEMICAL CO., LTD.) and water (4 ml) were added, the mixture solution was stirred, then the interior of the system was purged with hydrogen, and the system was allowed to react under a hydrogen atmosphere at 50° C. for 7 hours while stirring. After confirming the completion of the reaction, the reaction solution was purged with nitrogen and filtered to obtain a filtrate, and the residue was washed on the filter with THF (34 ml) to obtain a wash solution. The filtrate and the wash solution were combined, activated carbon (2.6 g, Japan Envirochemical Co., Ltd.) was added to the combined solution, and the mixture solution was stirred for 1 hour at room temperature. The suspension was filtered to obtain a filtrate, and the residue was washed on the filter with THF (34 ml) to obtain a wash solution. Then, the obtained filtrate and the wash solution were combined, water (207 ml) was added to the combined solution over 1 hour, and the mixture solution was stirred for another 1 hour under ice cooling. Then, this mixture solution was filtered, and the solids were washed on the filter with water (68 ml) to obtain wet solids. These wet solids were dried under reduced pressure at 50° C. to obtain crystals of the title compound (10.3 g).

Example 2-A, B

Preparation Example 2 for Compound 3 of the Invention

Crystals of the Compound 3 of the invention can be obtained by adding heptane to the combined solution of filtrate and wash solution instead of water as used in Example 2.

Furthermore, crystals of the Compound 3 of the invention can be obtained by using isopropanol as the solvent.

Example 3

Preparation Example 1 of Type A Crystal of Compound 1 of the Invention

Methanol (45 ml) was added to the Compound 3 of the invention (10.0 g) obtained in Example 2 and the solution was stirred. A 2 N aqueous solution of sodium hydroxide (17.0 ml) was added to the above solution and the mixture was stirred for 3 hours at 60° C. to perform alkali hydrolysis. After the reaction, the reaction solution was cooled to 35° C., and a 2 N aqueous solution of hydrochloric acid (17.0 ml) was added thereto over 2 hours, which was further stirred for 16 hours at 35° C. Then, this mixture solution was filtered, and the solids were washed on the filter with a mixture of water (27 ml) and methanol (13 ml) to obtain wet solids. These wet solids were dried under reduced pressure at 50° C. to obtain 9.2 g of crystals.

Example 4

Preparation Example 1 for Type B Crystal of Compound 1 of the Invention

Acetone (17 ml) was added to the type A crystals of Compound 1 of the invention (1.0 g) prepared according to Example 3 and the mixture was heated in a water bath at 60° C. to dissolve the crystals. Then, the solution was stirred overnight at room temperature. The generated precipitate was filtered and solids were obtained on the filter. Then, the solids were dried under reduced pressure at 50° C., to obtain 0.55 g of crystals.

Example 5

Preparation Example 2 for Type B Crystal of Compound 1 of the Invention

Dichloromethane (31 ml) was added to the type A crystals of Compound 1 of the invention (1.0 g) prepared according to Example 3, and the mixture was heated in a water bath at 40° C. to dissolve the crystals. Then, the solution was stirred overnight at room temperature. The generated precipitate was filtered, and solids were obtained on the filter. Then, the solids were dried under reduced pressure at 50° C. to obtain 0.81 g of crystals.

The crystals showed a spectrum which is substantially identical to FIG. 7 in a differential scanning calorimetric analysis according to Test Example 4 that will be described later, and thus were confirmed to be type B crystal of the Compound 1 of the invention.

Example 6

Preparation Example 3 for Type B Crystal of Compound 1 of the Invention

Methanol (45 ml) was added to the type A crystals of Compound 1 of the invention (10.0 g) prepared according to Example 3 and the mixture was stirred. Then, a 2 N aqueous solution of sodium hydroxide (17.0 ml) was added to the mixture, and the mixture solution was stirred for 1 hour at 60° C. This mixture solution was cooled to 35° C. and a 2 N aqueous solution of hydrochloric acid (7.0 ml) was added thereto over 30 minutes. After confirming that pH of the mixture solution reached 7 to 9, the seed crystals of the type B crystals of Compound 1 of the invention (0.1 g) prepared according to Example 4 were immediately added and the mixture solution was further stirred for 10 minutes. Then, a 2 N aqueous solution of hydrochloric acid (10.0 ml) was added to this mixture solution over 1 hour and the mixture solution was stirred for 2 hours at 35° C. Then, this mixture solution was filtered and the solids were washed on the filter with a mixture solution of water (27 ml) and methanol (13 ml) to obtain wet solids. These wet solids were dried under reduced pressure at 50° C. to obtain 9.7 g of white crystals.

The crystals showed a spectrum which is substantially identical to FIG. 6 in a powder X-ray diffraction measurement according to Test Example 3 that will be described later, and thus were confirmed to be type B crystal of the Compound 1 of the invention. Also, the crystals showed a spectrum which is substantially identical to FIG. 7 in a differential scanning calorimetric analysis according to Test Example 4 that will be described later, and thus were confirmed to be type B crystal of the Compound 1 of the invention.

Example 7

Preparation Example 4 for Type B Crystal of Compound 1 of the Invention

Methanol (360.0 ml) was added to the Compound 3 of the invention (80.0 g) obtained by a process in accordance with Example 2 and the mixture was stirred. Then, water (36.2 ml) and a 2 N aqueous solution of sodium hydroxide (99.7 ml) were added to the mixture, and the resultant solution was subjected to alkali hydrolysis while stirring at 60° C. for 3 hours. After the reaction, impurities such as fine dust in the reaction solution were separated by filtration, water (180.2 ml) was added, and then the mixture solution was adjusted to 35° C. A 2 N aqueous solution of hydrochloric acid (10.7 ml) was added to the mixture solution over 8 minutes, and after confirming that pH of the mixture solution reached 7.9, the seed crystals of the type B crystals of Compound 1 of the invention (0.08 g) prepared according to Example 4 were immediately added, and the resultant was stirred for 4 minutes. Then, a 2 N aqueous solution of hydrochloric acid (89.0 ml) was added to this mixture solution over 111 minutes and the solution was stirred for 14.3 hours at 35° C. Then, this mixture solution was filtered and solids were washed on the filter with a mixture solution of water (213.4 ml) and methanol (106.7 ml) to obtain wet solids. To these wet solids, water (213.4 ml) and methanol (106.7 ml) were added again to form a mixture solution, and stirred for 37 minutes at 18 to 20° C. Then, this mixture solution was filtered, and solids were washed on the filter with a mixture solution of water (21.3 ml) and methanol (10.7 ml) to obtain wet solids. These wet solids were dried under reduced pressure at 50° C. to obtain 76.28 g of white crystals.

These crystals showed a spectrum which is substantially identical to FIG. 7 in a differential scanning calorimetric analysis according to Test Example 4 that will be described later, and thus were confirmed to be type B crystal of the Compound 1 of the invention.

Example 8

Preparation Example 1 for Mixed Crystals of Compound 1 of the Invention 0.9 g type A crystals of the Compound 1 of the invention prepared according to Example 3 and 0.1 g of type B crystals prepared according to Example 4 were mixed using a mortar and a pestle, and a mixture containing 90% of type A crystals and 10% of type B crystals was obtained.

Example 9

Preparation Example 2 for Mixed Crystals of Compound 1 of the Invention 0.1 g of type A crystals of the Compound 1 of the invention prepared according to Example 3 and 0.9 g of type B crystals prepared according to Example 4 were mixed using a mortar and a pestle, and a mixture containing 10% of type A crystals and 90% of type B crystals was obtained.

Example 10

Preparation Example 2 for Type A Crystal of Compound 1 of the Invention

Compound 3 of the invention (3.92 kg) obtained by a method in accordance with Example 2 was introduced into a reaction apparatus A (instrument number: BD-1, 30 L elevation type reaction apparatus, ASAHI TECHNO GLASS CORPORATION), methanol (14.08 kg) was added thereto, and the mixture solution was stirred. After adding a 2 N aqueous solution of sodium hydroxide (6.76 kg), the mixture solution was heated to 60.6° C. over 27 minutes. The mixture solution was stirred at about 60° C. for 4 hours and 9 minutes, and then cooled to 35° C. over 19 minutes, and the reaction solution was filtered through a membrane filter to prepare a reaction solution 1. Furthermore, Compound 3 of the invention (3.92 kg) obtained according to a method in accordance with Example 2 was introduced into the reaction apparatus A, methanol (14.25 kg) was added thereto, and the mixture solution was stirred. After adding a 2 N aqueous solution of sodium hydroxide (6.70 kg), the mixture solution was heated to 60° C. over 30 minutes. The mixture solution was stirred at about 60° C. for 4 hours and 30 minutes, and then cooled to 34.6° C. over 17 minutes, the reaction solution was filtered through a membrane filter, and the filtrate was combined with the reaction solution 1 in a reaction apparatus B (instrument No.: BD-2, 100 L elevation type reaction apparatus, ASAHI TECHNO GLASS CORPORATION) to prepare a reaction solution 2. This reaction solution 2 was maintained at 30 to 35° C., and a 2 N aqueous solution of hydrochloric acid (13.30 kg) was added dropwise over 5 hours and 48 minutes while stirring to precipitate crystals, thus preparing a precipitate solution. Then, while maintaining this precipitate solution at about 35° C., the precipitate solution was stirred for 10 hours and 5 minutes, and then introduced into a filtering vessel (Instrument No.: F-9, ϕ600 mm Nutsche filter, ASAHI ENGINEERING CO., LTD.), and filtration by aspiration was performed to obtain wet crystals. To the wet crystals on this filtering vessel, a mixture solution of water (20.00 kg) and methanol (7.88 kg) was poured and aspirated, thus washing the wet crystals. Furthermore, aspiration was continued to sufficiently dehydrate, and wet crystals of the type A crystal of Compound 1 of the invention (15.571 kg) were obtained. At that time, the time required until wet crystals were obtained from the precipitate solution by filtration was 1 hour and 5 minutes, the time required for washing the wet crystals on the filtering vessel with a mixture solution of water and methanol was 1 hour and 44 minutes, and the time required for dehydration was 50 minutes. These wet crystals were spread on a tray and placed in a dryer (instrument No.: BM-6, compartment tray vacuum dryer, VAC-300PR, Espec Corporation), and dried under reduced pressure at 50° C. for 3 days (over 65 hours and 52 minutes), to obtain the type A crystals of Compound 1 of the invention (7.402 kg).

The crystals showed a spectrum which is substantially identical to FIG. 3 in a powder X-ray diffraction measurement according to Test Example 3 that will be described later, and thus were confirmed to be type A crystal of the Compound 1 of the invention. Also, the crystals showed a spectrum which is substantially identical to FIG. 4 in a differential scanning calorimetric analysis according to Test Example 4 that will be described later, and thus were confirmed to be type A crystal of the Compound 1 of the invention.

Example 11

Preparation Example 5 for Type B Crystal of Compound 1 of the Invention

Compound 3 of the invention (3.90 kg) obtained by a method in accordance with Example 2 was introduced into a reaction apparatus A (instrument number: BD-1, 30 L elevation type reaction apparatus, ASAHI TECHNO GLASS CORPORATION), methanol (13.75 kg) was added thereto, and the mixture solution was stirred. After adding a 2 N aqueous solution of sodium hydroxide (5.20 kg) and water (1.75 kg), the mixture solution was heated to 60° C. over 42 minutes. The mixture solution was stirred at about 60° C. for 2 hours and 29 minutes, and then cooled to 35.0° C. over 13 minutes, and the reaction solution was filtered through a membrane filter to prepare a reaction solution 1. Furthermore, Compound 3 of the invention (3.90 kg) obtained by a method in accordance with Example 2 was introduced into the reaction apparatus A, methanol (13.97 kg) was added thereto, and the mixture solution was stirred. After adding a 2 N aqueous solution of sodium hydroxide (5.20 kg) and water (1.75 kg), the mixture solution was heated to 60° C. over 40 minutes. The mixture solution was stirred at about 60° C. for 2 hours and 34 minutes, and then cooled to 35.0° C. over 19 minutes, and the reaction solution was filtered through a membrane filter, and the filtrate was combined with the reaction solution 1 in a reaction apparatus B (instrument No.: BD-2, 100 L elevation type reaction apparatus, ASAHI TECHNO GLASS CORPORATION) to prepare a reaction solution 2. After adding water (17.36 kg) to the reaction solution 2, this reaction solution 2 was maintained at 30 to 35° C., a 2 N aqueous solution of hydrochloric acid (0.92 kg) was added dropwise over 38 minutes with stirring, and dropwise addition was stopped at a time point that pH reached 7.90. Then, type B crystals of the Compound 1 of the invention (7.795 g) were added, and then a 2 N aqueous solution of hydrochloric acid (9.08 kg) was added dropwise over 3 hours and 50 minutes, thus to precipitate crystals out and to prepare a precipitate solution. Further, this precipitate solution was stirred for 8 hours and 42 minutes while maintaining at about 35° C., and then was introduced into a filtering vessel (instrument No.: F-9, ϕ600 mm Nutsche filter, ASAHI ENGINEERING CO., LTD.), and filtration by aspiration was performed in the same manner as in Example 10 to obtain wet crystals. To the wet crystals on this filtering vessel, a mixture of water (20.78 kg) and methanol (8.10 kg) was poured and aspirated to wash the wet crystals. Furthermore, aspiration was continued to sufficiently dehydrate, and wet crystals of the type B crystal of Compound 1 of the invention were obtained. At this time, the time required until wet crystals were obtained from the precipitate solution by filtration was 8 minutes, the time required for washing the wet crystals on the filtering vessel with a mixture of water and methanol was 10 minutes, and the time required for dehydration was 37 minutes. In order to increase the purity of these wet crystals, a mixture of water (21.00 kg) and methanol (8.18 kg) was added to obtain a suspension, and the suspension was stirred for 34 minutes and washed. Then, this suspension was introduced into a filtering vessel (instrument No.: F-9, ϕ600 mm Nutsche filter, ASAHI ENGINEERING CO., LTD.). Then, a mixture solution of water (2.10 kg) and methanol (0.80 kg) was introduced into the filtering vessel, and filtration by aspiration was performed to obtain wet crystals. Then, aspiration was continued to sufficiently dehydrate, thus to obtain wet crystals of the type B crystal of Compound 1 of the invention (12.211 kg). At this time, the time required until wet crystals were obtained from the suspension by filtration was 4 minutes, and the time required in dehydration was 16 minutes. These wet crystals were spread on a tray and placed in a dryer (instrument No.: BM-6, compartment tray vacuum dryer, VAC-300PR, Espec Corporation), and dried under reduced pressure at 50° C. for 3 days (over 71 hours and 3 minutes) to obtain the type B crystals of Compound 1 of the invention (7.412 kg).

The crystals showed a spectrum which is substantially identical to FIG. 6 in a powder X-ray diffraction measurement according to Test Example 3 that will be described later, and thus were confirmed to be type B crystal of the Compound 1 of the invention. Further, the crystals showed a spectrum which is substantially identical to FIG. 7 in a differential scanning calorimetric analysis according to Test Example 4 that will be described later, and thus were confirmed to be type B crystal of the Compound 1 of the invention.

Test Example 1

Measurement of Rate of Filtration 1

To the type A crystals of Compound 1 of the invention (5.0 g) prepared according to Example 3, a mixture solution of methanol and water (mixing ratio 1:2) (50 ml) was added, the resultant was stirred for 30 minutes at 25° C., and then a Kiriyama funnel (internal diameter 40 mm, filter paper for Kiriyama funnel No. 3) and an aspirator were used for filtration. At that time, it required 2 minutes and 37 seconds for obtaining 10 ml of a filtrate, it required 7 minutes and 45 seconds for obtaining 20 ml of a filtrate, it required 15 minutes and 14 seconds for obtaining 30 ml of a filtrate, and finally it required 25 minutes and 24 seconds to obtain 40 ml of a filtrate. Also, the wet solids on the funnel were dried under reduced pressure at 50° C. to obtain 4.9 g of crystals.

To the type B crystals of Compound 1 of the present invention (5.0 g) prepared according to Example 4, a mixed solution (50 ml) of methanol:water (1:2) was added, the resultant was stirred for 30 minutes at 25° C., and filtration was performed using a Kiriyama funnel (internal diameter 40 mm, filter paper for Kiriyama funnel No. 3) and an aspirator were used for filtration. At that time, it required 8 seconds for obtaining 10 ml of a filtrate, it required 17 seconds for obtaining 20 ml of a filtrate, it required 28 seconds for obtaining 30 ml of a filtrate, and finally it required 2 minutes to obtain 42 ml of a filtrate. Also, the wet solids on the funnel were dried under reduced pressure at 50° C. to obtain 4.7 g of crystals.

As described above, the time required for obtaining type B crystals may be one-tenth or less compared with the time required for obtaining type A crystals, and thus, excellent filterability of the type B crystal of the present invention was confirmed.

Test Example 1-2

Measurement of Rate of Filtration 2

The filterability of the type A crystal of Compound 1 of the invention in Example 10 was compared with the filterability of the type B crystal of Compound 1 of the invention in Example 11. For each of them, the period of times required in three steps, such as (1) the time required for separating wet crystals form the mother liquor by aspiration from the introduction of the precipitate solution into a filtering vessel, (2) then, the time required for washing the set crystals in the filtering vessel by aspiration from the introduction of a washing mixture of water and methanol, and (3) finally, the time required for sufficiently reducing the moisture of the wet crystals by continued aspiration from the end of the washing, were compared. For the type A crystals, it took (1) 1 hour 5 minutes, (2) 1 hour 44 minutes, and (3) 50 minutes, while for the type B crystals, it took (1) 8 minute, (2) 10 minutes and (4) 37 minutes. Thus, the excellent filterability of the type B crystal of the invention could be confirmed.

Test Example 1-3

Measurement of Water Content After Filtration

The respective water contents of the crystals obtained in Example 10 and Example 11 were calculated from the weight of the wet crystals and the weight of the crystals after drying. The water contents were 52.5% and 39.3% for the type A crystal and the type B crystal, respectively. Thus, the drying properties of the type B crystal of the present invention were excellent. The results are presented in Table 1. In Example 10 and Example 11, both of them were dried for 3 days, but in practice, it can be easily conjectured that the type B crystal having low water content would require less time and energy for drying.

TABLE 1

Measurement results for water content

| Crystal | Weight of wet crystals (kg) | Weight of crystals after drying (kg) | Water content (%) |
| --- | --- | --- | --- |
| Type A crystal (Example 10) | 15.571 | 7.402 | 52.5 |
| Type B crystal (Example 11) | 12.211 | 7.412 | 39.3 |

Test Example 2

Solubility Test

The type A crystals of compound 1 of the invention prepared according to Example 3, and the type B crystals of compound 1 of the invention prepared according to Example 4 were respectively weighed to 10 mg in a 10-mL centrifuge tube, 3 mL each of 1st fluid for disintegration test of Japanese Pharmacopoeia (pH 1.2) was added respectively, and the mixture solutions were shaken for 24 hours at 37° C. After the shaking, the solutions were filtered, 1 mL of each filtrate was exactly pipeted, and 1 mL of acetonitrile was exactly added to obtain a sample solution.

The sample solutions were analyzed by using HPLC technique with the following conditions and the concentration of the compound in the sample solution was determined by comparing it with that of a standard solution having an already known concentration under the following HPLC conditions, to determine the solubility.

The same test was performed with 2nd fluid for disintegration test of Japanese Pharmacopoeia (pH 6.8), to determine the solubility.

The results are presented in Table 2.

Conditions

Injection volume: 10 µL

Detector: Ultraviolet absorption spectrometer (wavelength: 235 nm)

Mobile phase: 50 mmol/L sodium dihydrogen phosphate/acetonitrile (55:45)

Column: YMC-Pack Pro C18, internal diameter: 4.6 mm, length: 15 cm (YMC Corporation)

Column temperature: 40° C.

Flow rate: 1.0 mL/min

TABLE 2

Solubility test results

| Crystal | Solubility to 1st fluid for disintegration test of Japanese Pharmacopoeia (pH 1.2) (mg/mL) | Solubility to 2nd fluid for disintegration test of Japanese Pharmacopoeia (pH 6.8) (mg/mL) |
| --- | --- | --- |
| Type A crystal | 0.03 | 0.06 |
| Type B crystal | 0.01 | 0.02 |

As shown in Table 2, the solubilities of the type A crystal to 1st fluid for disintegration test of Japanese Pharmacopoeia (pH 1.2) and 2nd fluid for disintegration test of Japanese Pharmacopoeia (PH 6.8) were three-fold greater than those of the type B crystals, and the high solubility of the type A crystal of the present invention could be confirmed.

Test Example 3

Powder X-Ray Diffraction

Powder X-ray diffraction analysis was conducted for the crystals obtained in the respective Examples of the present specification.

Measurement Conditions

X-ray diffraction apparatus: XRD-6000 manufactured by SHIMADZU CORPORATION
X-ray source: CuKα (40 kV, 30 mA)
Scan mode: continuous
Scan rate: 2°/min
Scanning step: 0.02°
Scan driving axis: θ-2θ
Scan range: 5° to 40°
Scattering slit: 1°
Incident slit: 0.30 mm The results of the measurement are as follows.

Crystals of the Compound 2 of the invention obtained by a method in accordance with Example 1 were measured, and the spectrum shown in FIG. 1 was obtained. For the powder X-ray diffraction spectrum of the crystals of Compound 2 of the invention, characteristic peaks were observed at 2θ of 7.6°, 15.3°, 18.0°, 21.3° and 26.9°. Peaks were also observed at any or all of 16.3°, 20.4°, 23.0° or 30.5°, and any of these can also be construed at least as characteristic peaks. Furthermore, peaks were also observed at any or all of 11.5°, 19.1°, 25.1° or 25.8°, and any of these can also be construed at least as characteristic peaks. These crystals were judged to be crystals even from morphological observation with naked eyes, and it was also confirmed from the analysis data described above that they were crystals.

Figure 2:
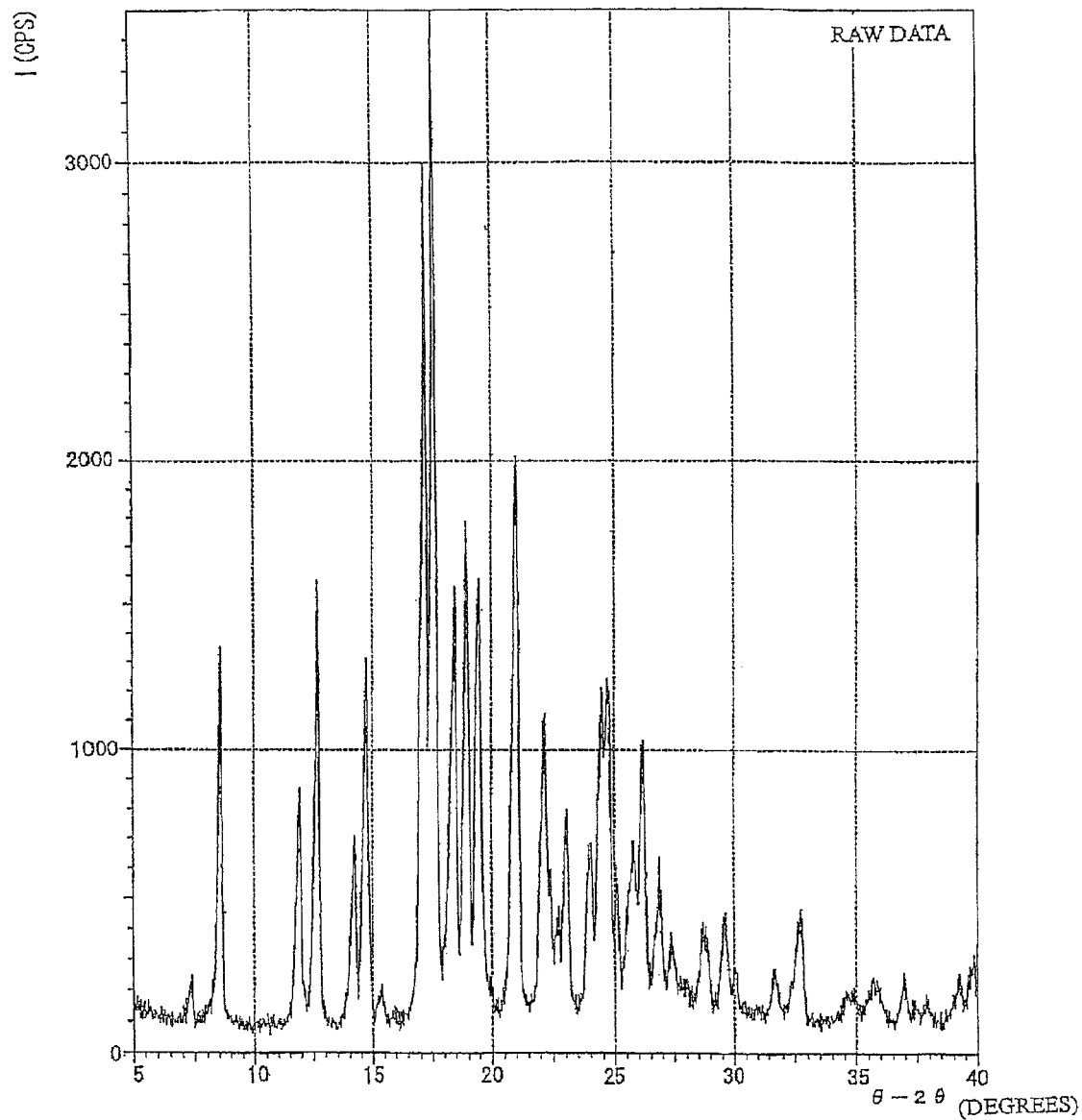
FIG. 2 is a powder X-ray diffraction spectrum of the crystals of Compound 3 of the invention. In the diagram, the vertical axis indicates intensity (CPS), and the horizontal axis indicates 2θ (°).

Further, crystals of the Compound 3 of the invention obtained by a method in accordance with Example 2 were measured, and the spectrum shown in FIG. 2 was obtained. For the powder X-ray diffraction spectrum of the crystals of Compound 3 of the invention, characteristic peaks were observed at 2θ of 8.6°, 12.7°, 17.2°, 17.6°, 18.9° and 21.0°. Peaks were also observed at any or all of 14.7°, 18.4°, 19.4° or 22.1°, and any of these can also be construed at least as characteristic peaks. Furthermore, peaks were also observed at any or all of 11.9°, 14.2°, 23.0°, 24.7°, 26.1°, 26.8° or 32.6°, and any of these can also be construed at least as characteristic peaks. These crystals were judged to be crystals even from morphological observation with naked eyes, and it was also confirmed from the analysis data described above that they were crystals.

Figure 3:
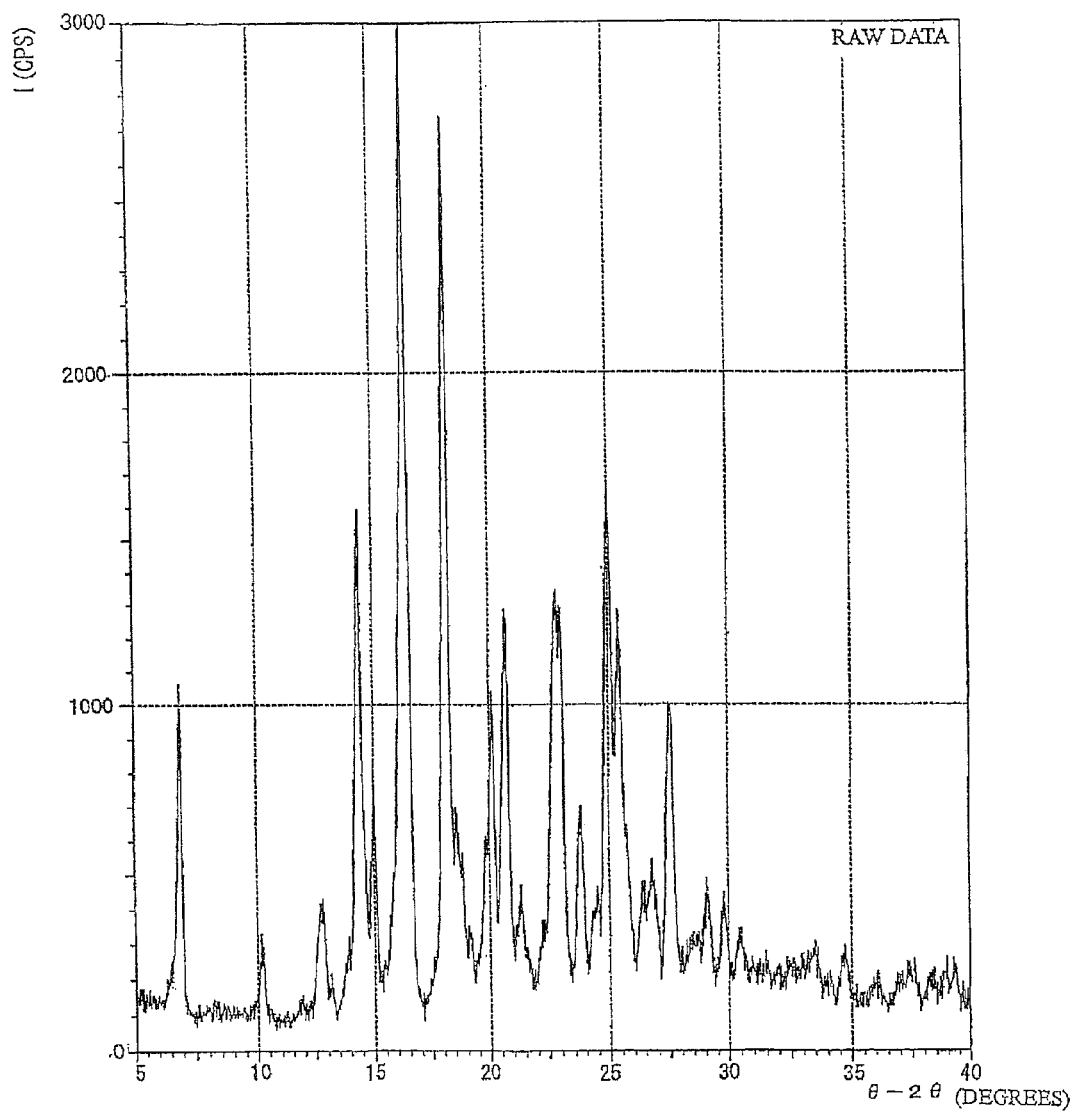
FIG. 3 is a powder X-ray diffraction spectrum of type A crystals of Compound 1 of the invention. In the diagram, the vertical axis indicates intensity (CPS), and the horizontal axis indicates 2θ (°).

Type A crystals of the Compound 1 of the invention obtained by a method in accordance with Example 3 were measured, and the spectrum shown in FIG. 3 was obtained. For the powder X-ray diffraction spectrum of the type A crystals of Compound 1 of the invention, characteristic peaks were observed at 2θ of 6.9°, 14.4°, 16.4°, 18.2°, 25.0° and 27.5°. Peaks were also observed at any or all of 20.0°, 20.7°, 22.9° or 25.4°, and any of these can also be construed at least as characteristic peaks. Furthermore, peaks were also observed at any or all of 10.2°, 12.7°, 15.0° or 23.8°, and any of these can also be construed at least as characteristic peaks.

Figure 6:
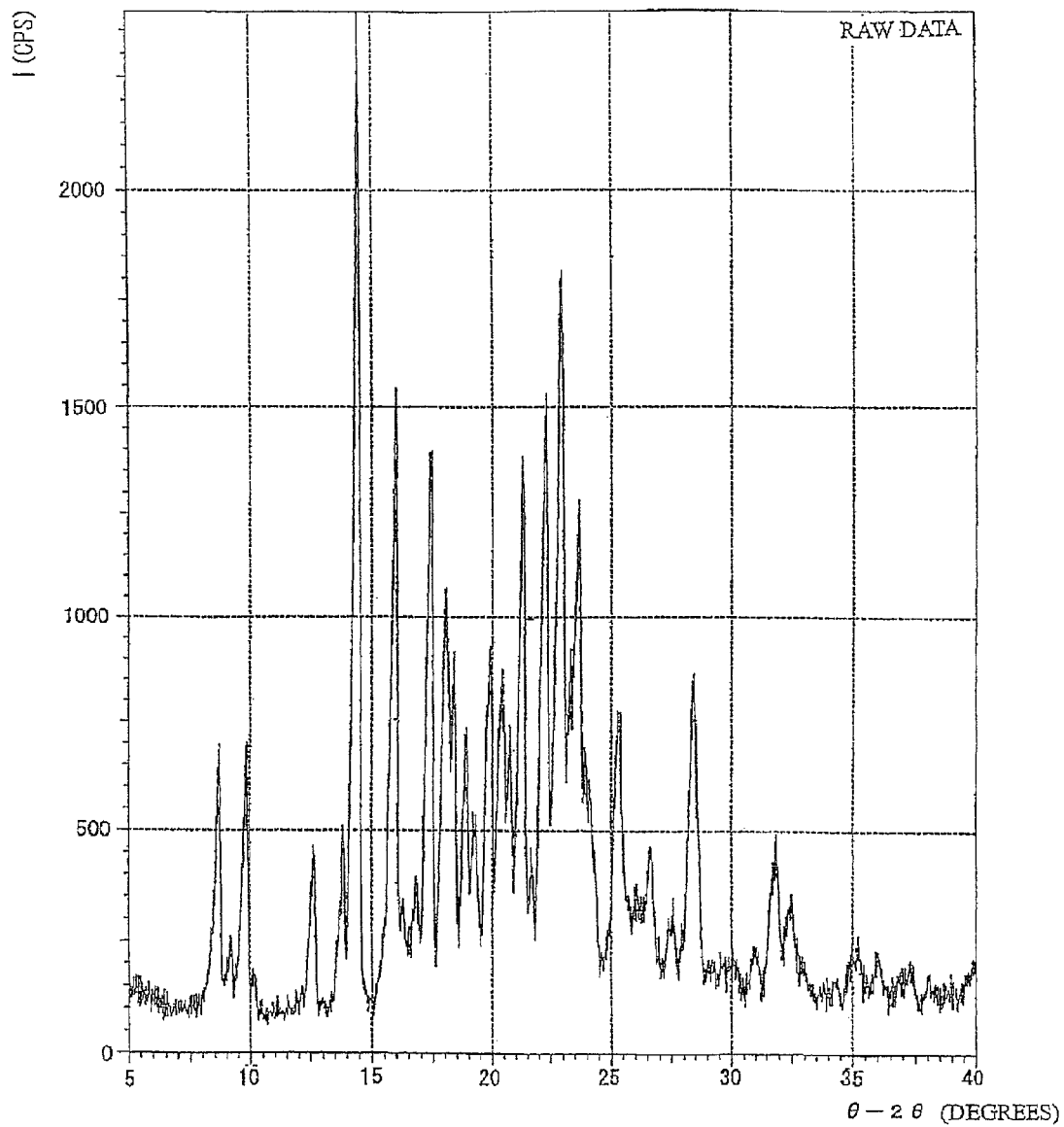
FIG. 6 is a powder X-ray diffraction spectrum of type B crystals of Compound 1 of the invention. In the diagram, the vertical axis indicates intensity (CPS), and the horizontal axis indicates 2θ (°).

Type B crystals of the Compound 1 of the invention obtained by a method in accordance with Example 6 were measured, and the spectrum shown in FIG. 6 was obtained. For the powder X-ray diffraction spectrum of the type B crystals of Compound 1 of the invention, characteristic peaks were observed at 2θ of 14.4°, 15.9°, 17.3°, 22.2° and 22.9°. Peaks were also observed at any or all of 8.6°, 9.8°, 21.2°, 23.6° or 28.4°, and any of these can also be construed at least as characteristic peaks. Furthermore, peaks were also observed at any or all of 12.6°, 18.0°, 18.3°, 18.8°, 19.2°, 19.8°, 20.4°, 25.3°, 26.6° or 31.8°, and any of these can also be construed at least as characteristic peaks.

Test Example 3-2

Method for Measurement of Crystal Purity

When calculating the rate of contamination in the case of one crystal type of Compound 1 of the invention contaminates the other type of crystal, it is suggested to perform a powder X-ray diffraction spectroscopic measurement under the following conditions which uses a parallel beam optical system which with a rotating sample stage. Specifically describing by taking an example of the case in which type A crystal contaminates type B crystals, type A crystals which are pure as crystals are used as the standard material and an appropriate peak is selected from the characteristic peaks of the type A crystal (the appropriate peak may be exemplified by a peak at 6.9±0.2°. With respect to that peak, the peak intensity of the standard material and the peak intensity of a sample to be measured are compared; that is, the peak intensity of the sample to be measured is divided by the peak intensity of the standard material, thereby the rate of the contamination of the type A crystals in the sample can be calculated.

Measurement Conditions

X-ray diffraction apparatus: RINT 2200 Ultima+/PC manufactured by Rigaku Corporation
Measurement method: Parallel beam method, using rotating sample stage
X-ray source: CuKα (40 kV, 50 mA)
Scan mode: continuous
Scan rate: 2°/min
Scanning step: 0.02°
Scan driving axis: θ-2θ
Scan range: 3° to 40°
Scattering slit: open
Incident slit: open
Speed of rotation of sample stage: 120 rpm

Test Example 4

Differential Scanning Calorimetric Analysis 1 to 3 mg of the crystals obtained in Example 3 or 4 of the present specification were placed in an open aluminum pan, and measurement was performed in a dry nitrogen atmosphere from 50° C. to 220° C. at a heating rate of 10° C./min, using a PYRIS Diamond DSC differential scanning calorimetric measurement apparatus manufactured by PerkinElmer, Inc. Alternatively, measurement was performed from 50° C. to 220° C. at a heat rate of 10° C./min, using a DSC3200 DSC differential scanning calorimetric measurement apparatus manufactured by Bruker AXS K.K.

The results are as follows.

Figure 4:
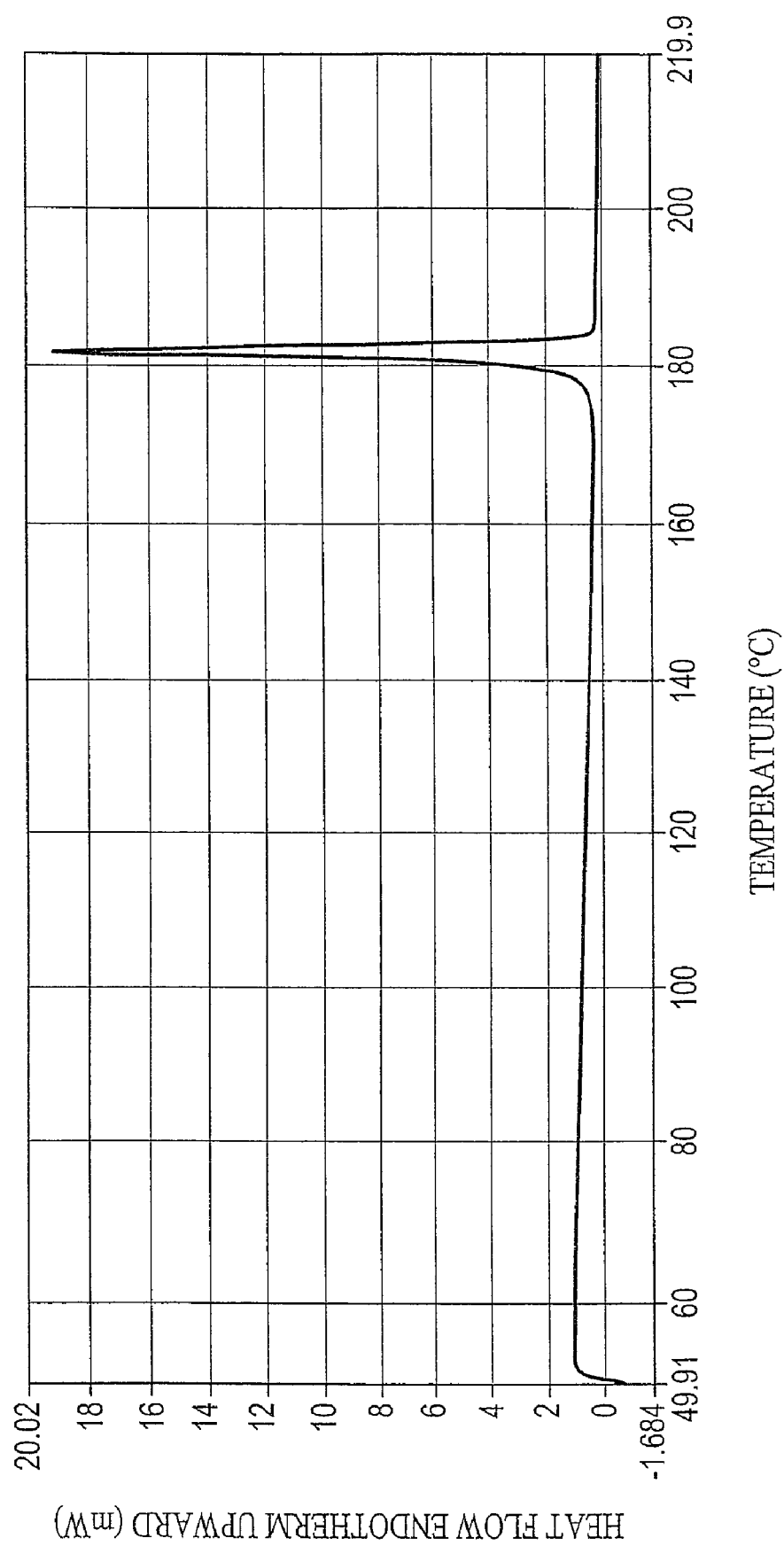
FIG. 4 is a differential scanning calorimetric analysis of type A crystals of Compound 1 of the invention. In the diagram, the vertical axis indicates mW, and the horizontal axis indicates temperature (° C.).

Measurement was made with the type A crystals of Compound 1 of the invention obtained by a method in accordance with Example 3, and as a result, the chart shown in FIG. 4 was obtained. In the differential scanning calorimetric analysis of the type A crystals of the Compound 1 of the invention, an endothermic peak was observed at about 182° C. Additionally, any particular peak suggesting the existence of a hydrate or a solvate was not observed.

Figure 7:
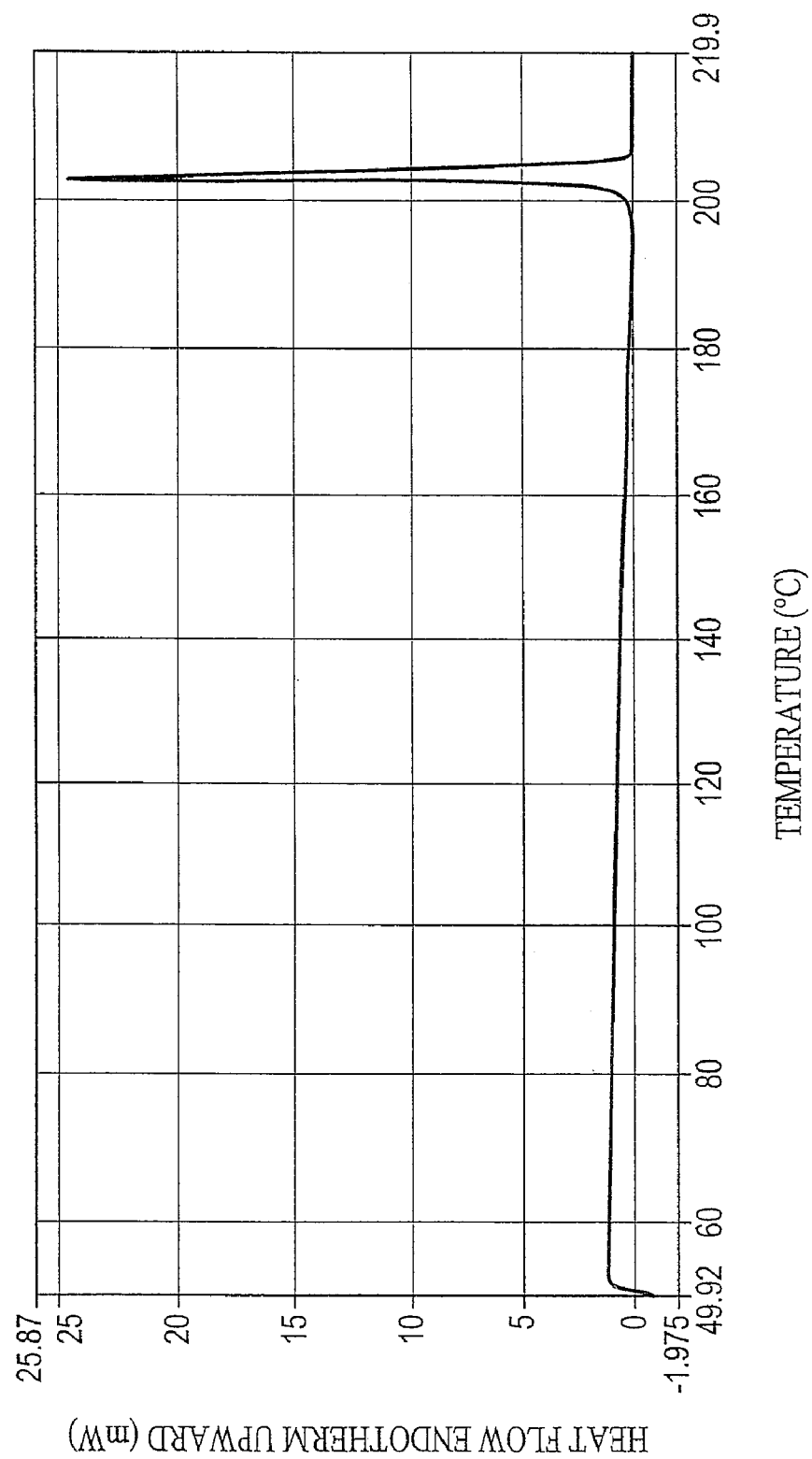
FIG. 7 is a differential scanning calorimetric analysis of type B crystals of Compound 1 of the invention. In the diagram, the vertical axis indicates mW, and the horizontal axis indicates temperature (° C.).

Furthermore, measurement was made with the type B crystals of the Compound 1 of the invention obtained by a method in accordance with Example 4, and as a result, the chart shown in FIG. 7 was obtained. In the differential scanning calorimetric analysis of the type B crystals of the Compound 1 of the invention, an endothermic peak was observed at about 203° C. Additionally, any particular peak suggesting the existence of a hydrate or a solvate was not observed.

Moreover, it was found that the chart of the crystals prepared in Example 10 was substantially identical to FIG. 4, and thus they were the type A crystal. Also, the charts of the crystals prepared in Examples 5 to 7 and 11, respectively, were also substantially identical to FIG. 7, and it was suggested that they were the type B crystal.

According to the present invention, there is no particularly problem if the compounds of the invention are in the form of hydrate or solvate, but it is more preferable that they are anhydrides or non-solvates.

Test Example 5

Infrared Absorption Spectroscopic Analysis

With regard to the crystals obtained by methods in accordance with Example 3 or 6 of the present specification, measurement was made by a potassium bromide disk method.

The results are as follows.

Figure 5:
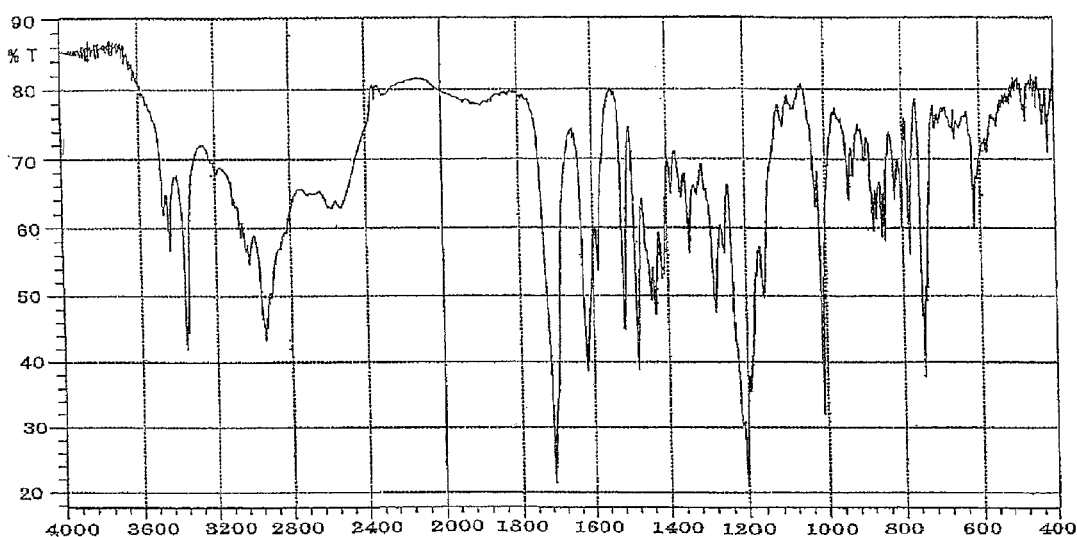
FIG. 5 is an infrared absorption spectrum of type A crystals of Compound 1 of the invention. In the diagram, the vertical axis indicates transmittance (%), and the horizontal axis indicates cm$^{-1}$.

Measurement was made with the type A crystals of Compound 1 of the invention obtained by a method in accordance with Example 3, and as a result, a spectrum shown in FIG. 5 was obtained. As a result, in the infrared absorption spectrum of the type A crystals of Compound 1 of the invention, significant infrared absorption bands were observed at wavenumbers 3361, 2938, 1712, 1204, 1011 and 746 cm$^{-1}$. Infrared absorption bands were also observed at any or all of 3443, 3349, 1620, 1515, 1480 or 1278 cm$^{-1}$, and any of these can also be construed at least as characteristic peaks. Furthermore, infrared absorption bands were also observed at any or all of 3473, 1585, 1432, 1343, 1159, 781 or 615 cm$^{-1}$, and any of these can also be construed at least as characteristic peaks.

Figure 8:
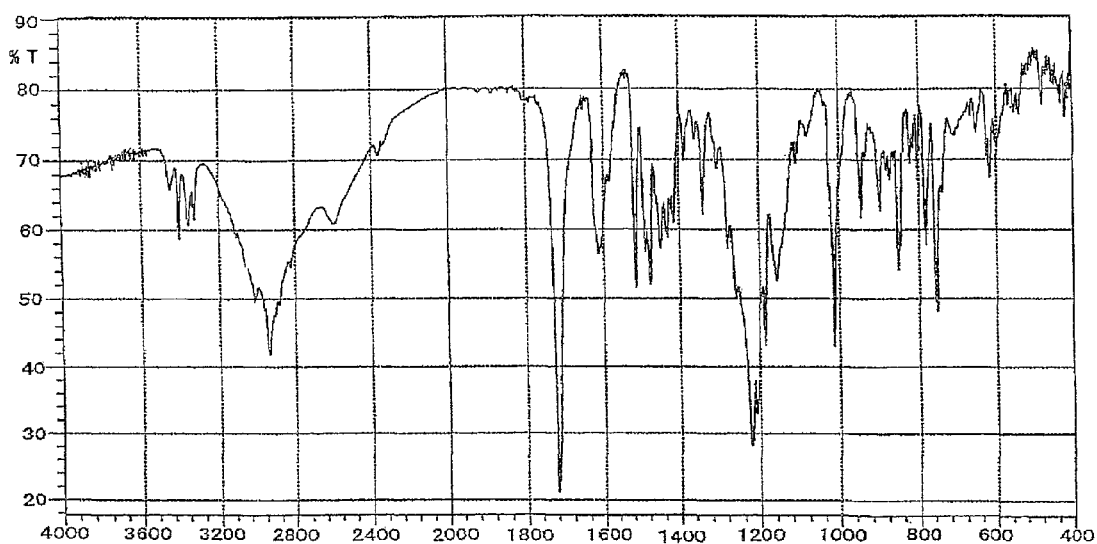
FIG. 8 is an infrared absorption spectrum of type B crystals of Compound 1 of the invention. In the diagram, the vertical axis indicates transmittance (%), and the horizontal axis indicates cm$^{-1}$.

Furthermore, measurement was made with the type B crystals of Compound 1 of the invention obtained by a method in accordance with Example 6, and as a result, a spectrum shown in FIG. 8 was obtained. As a result, in the infrared absorption spectrum of the type B crystals, significant infrared absorption bands were observed at wavenumbers 2939, 1720, 1224, 1016 and 751 cm$^{-1}$. Infrared absorption bands were also observed at any or all of 3407, 3358, 1513, 1476 or 852 cm$^{-1}$, and any of these can also be construed at least as characteristic peaks. Furthermore, infrared absorption bands were also observed at any or all of 3447, 3325, 1615, 1339, 1157, 945, 783 and 617 cm$^{-1}$, and any of these can also be construed at least as characteristic peaks.

Test Example 6

Quantitative Measurement of Crystals 0.4, 0.8, 1.2, 1.6, 2.0, 2.4, 2.8 or 3.2 mg of a standard material of the type A crystal of Compound 1 of the invention was placed in an open aluminum pan, and measurement was made in a dry nitrogen atmosphere from 50° C. to 220° C. at a heating rate of 50° C./min, using a PYRIS Diamond DSC differential scanning calorimetric measurement apparatus manufactured by PerkinElmer, Inc. Thus, the area (mJ) of an endothermic peak at around 185° C. was determined, and a calibration curve for quantification of the type A crystals was prepared.

Also, 0.4, 0.8, 1.2, 1.6, 2.0, 2.4, 2.8 or 3.2 mg of a standard material of the type B crystal of Compound 1 of the invention was placed in an open aluminum pan, and measurement was made in a dry nitrogen atmosphere from 50° C. to 220° C. at a heating rate of 50° C./min, using a PYRIS Diamond DSC differential scanning calorimetric measurement apparatus manufactured by PerkinElmer, Inc. Thus, the area (mJ) of an endothermic peak at around 205° C. was determined, and a calibration curve for quantification of the type B crystals was prepared.

Figure 9:
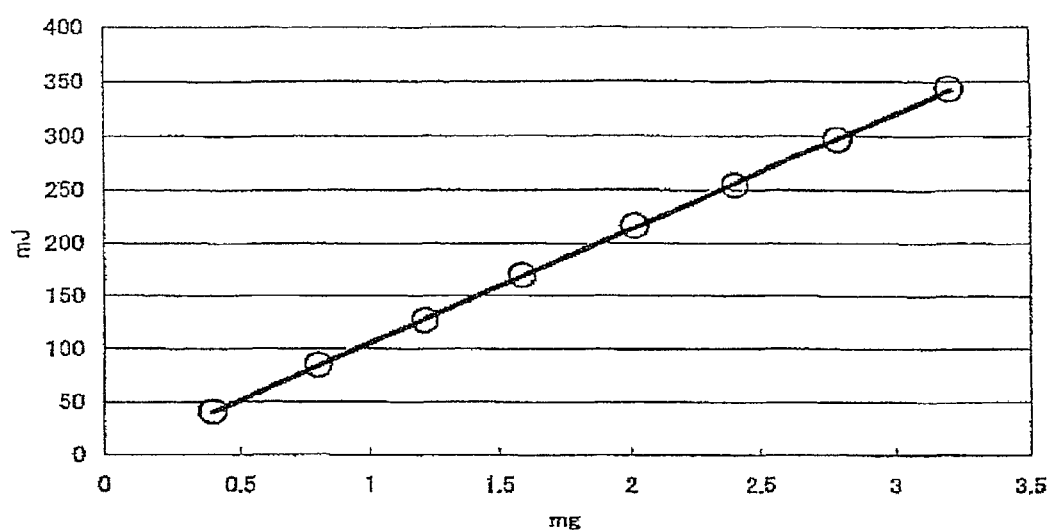
FIG. 9 shows a calibration curve for the differential scanning calorimetric analysis of type A crystals of Compound 1 of the invention. In the diagram, the vertical axis indicates area (mJ), and the horizontal axis indicates weight (mg).

The calibration curve for the type A crystal is shown in FIG. 9.

Figure 10:
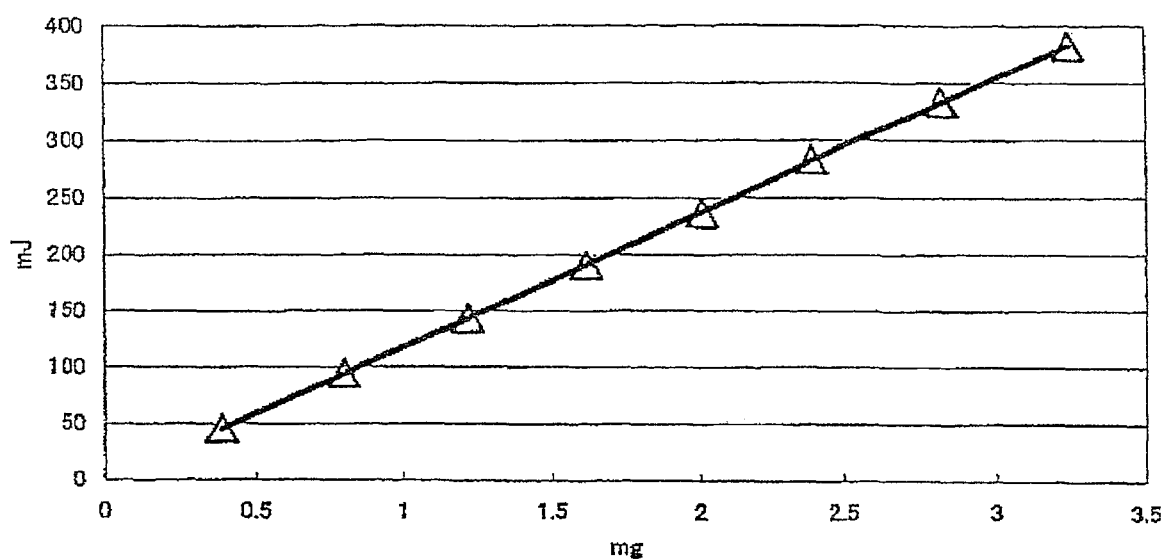
FIG. 10 shows a calibration curve for the differential scanning calorimetric analysis of type B crystals of Compound 1 of the invention. In the diagram, the vertical axis indicates area (mJ), and the horizontal axis indicates weight (mg).

Also, the calibration curve for the type B crystal is shown in FIG. 10.

It was verified that quantification was possible with both the type A crystals and the type B crystals.

Additionally, as the standard material of the type A crystal, measurement was performed using crystals which were obtained according to the method of Example 3 of the present specification, had a preferred shape in particular, and showed a characteristic single endothermic peak in differential scanning calorimetric analysis.

Also, as the standard material of the type B crystal, measurement was performed using crystals which were obtained according to the method of Example 4 of the present specification, had a preferred shape in particular, and showed a characteristic single endothermic peak in differential scanning calorimetric analysis.

Test Example 7

Quantification of Compounds of the Invention

Detection and quantification of the compounds of the invention were performed under the following HPLC conditions.

Conditions

Sample concentration: 0.2 mg/mL (Compounds 1 and 3 of the invention: dissolved in a mixture solution of water/acetonitrile (1:1)

Compound 2 of the invention: dissolved in acetonitrile)

Injection volume: 10 µL

Detector: Ultraviolet absorption spectrometer (wavelength: 235 nm)

Column: YMC-Pack Pro C18, internal diameter: 4.6 mm, length: 15 cm (YMC Corporation)

Column temperature: 40° C.

Mobile phase A: 50 mmol/L sodium dihydrogen phosphate

Mobile phase B: acetonitrile

Gradient program: The concentration gradient is controlled by changing the mixing ratio of mobile phase A and mobile phase B as shown in Table 3.

Flow rate: 1.0 mL/min

TABLE 3

| Gradient program | | |
|---|---|---|
| Time lapse after injection (min) | Mobile phase A (%) | Mobile phase B (%) |
| 0-45 | 65 → 20 | 35 → 80 |
| 45-60 | 65 | 35 |

As a result, as the retention time, peaks were observed at about 15 minutes for the Compound 1 of the invention, at about 30 minutes for the Compound 2 of the invention, and at about 25 minutes for the Compound 3 of the invention.

Calibration curves were obtained using known amounts of the respective standard materials of the compounds of the invention. The calibration curves showed linearity.

It was confirmed that quantitative measurement is possible for the compounds of the invention by the HPLC conditions of the present invention.

Test Example 8

Effect of Suppressing Production of $PGE_2$ from IL-1β Stimulated MG-63 Cells

For the compounds of the invention, the effect on suppressing the production of $PGE_2$ caused by Interleukin (IL)-1β, which is an inflammatory stimulating material, was investigated according to the method of International Patent Publication No. WO 03/70686.

As a result, all of the compounds obtained by the methods described in Examples 1 to 9 suppressed the production of $PGE_2$ caused by IL-1β, by 50% or more at 0.1 μM. Furthermore, no cytotoxic effect on the cells was observed for any of the test compounds at this concentration. Therefore, the compounds of the invention are useful as inhibitory drugs against the production of inflammatory prostaglandin.

Test Example 9

Prophylactic and Therapeutic Effect Against Rat Adjuvant Arthritis

For the compounds of the invention, a suppressive effect against footpad edema in rat adjuvant arthritis, which is a disease model for chronic rheumatoid arthritis as being one of autoimmune diseases and also a chronic inflammatory disease, was investigated according to the method of International Patent Publication No. WO 03/70686. The test compound was suspended in purified water containing 0.5% methylcellulose, and was orally administered to test animals at a dose of 0.1 to 50 mg/0.2 ml/kg.

As a result, both of the compounds obtained in Example 3 and Example 6 suppressed footpad edema in rat adjuvant arthritis, compared with the positive control group.

Also, during the present test, no mortality in the test animals was observed. Therefore, the compounds of the invention are useful as prophylactic and/or therapeutic drugs for chronic rheumatoid arthritis and autoimmune diseases.

Test Example 10

Scanning Electron Microscopic (SEM) Observation

The crystals obtained in Example 3 or 4 of the present specification were observed with observation.

Figure 11:
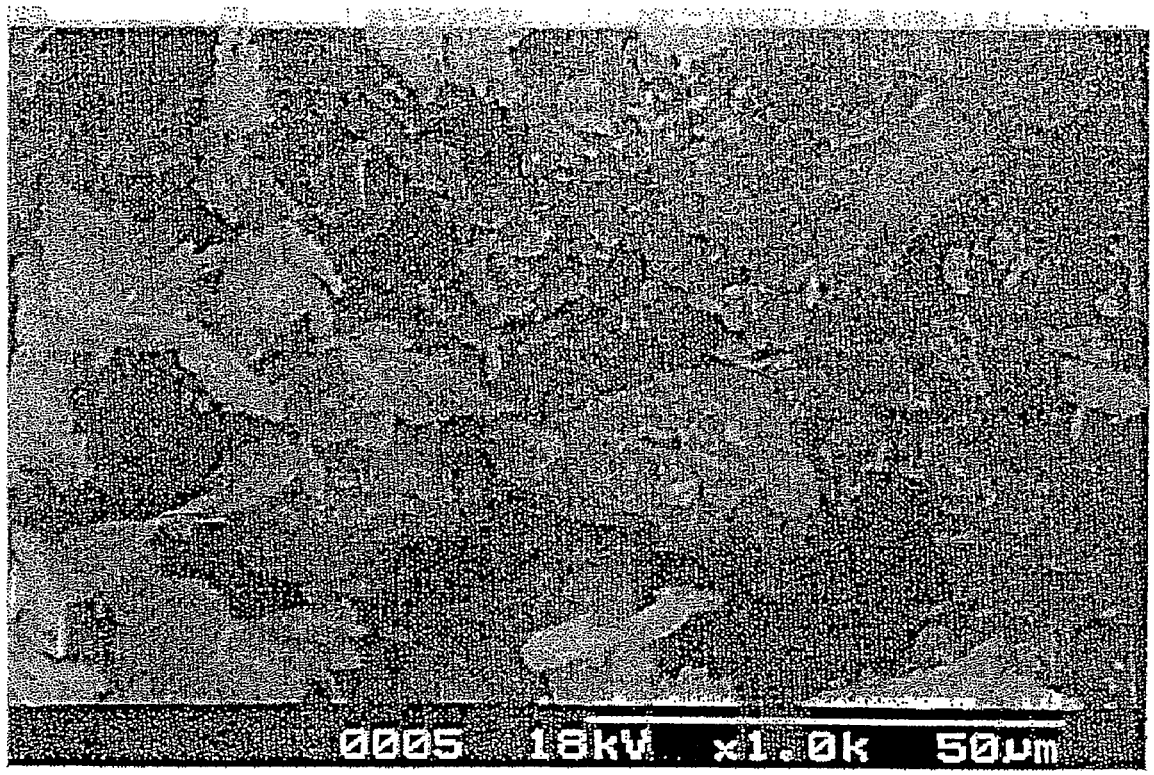
FIG. 11 is a scanning electron microscopic (SEM) photograph, which is a photograph showing the crystal shape of type A crystals of Compound 1 of the invention.

Measurement was made with the type A crystals of Compound 1 of the invention of Example 3, and as a result, a SEM photograph shown in FIG. 11 was obtained.

Figure 12:
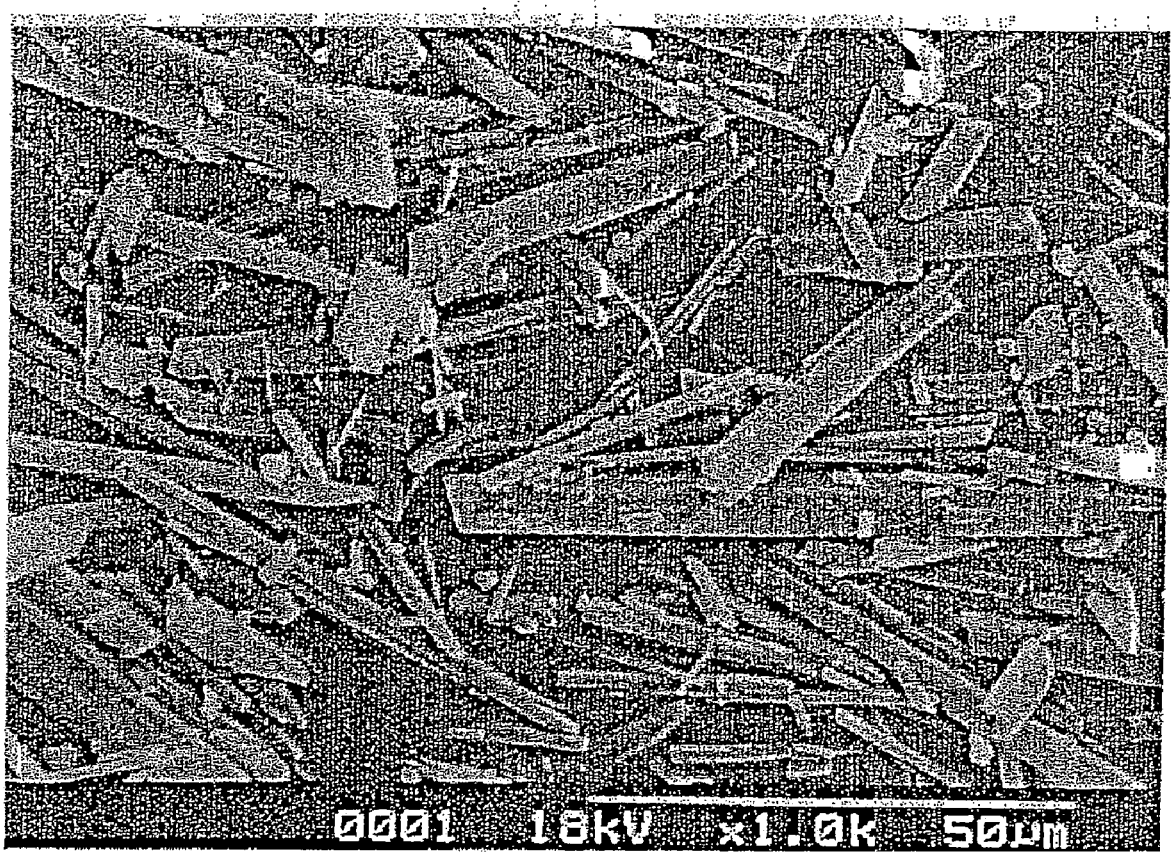
FIG. 12 is a scanning electron microscopic (SEM) photograph, which is a photograph showing the crystal shape of type B crystals of Compound 1 of the invention.

Measurement was made with the type B crystals of Compound 1 of the invention of Example 4, and as a result, a SEM photograph shown in FIG. 12 was obtained.

Nevertheless, these photographs are presented only for referential purposes, and the properties of any of the crystals of the present invention are neither intended to be defined by the electron microscopic images, nor need not be limited thereto.

The invention claimed is:

1. A crystal of methyl 3-[4-(indan-2-yloxy)-3-(1-methyl-1H-indazol-5-yl)-5-nitrophenyl]propionate wherein the crystal exhibits characteristic peaks at 2θ of 7.6±0.2°, 15.3±0.2°, 18.0±0.2°, 21.3±0.2° and 26.9±0.2° in a powder X-ray diffraction spectrum.

2. A dry pharmaceutical composition comprising: the crystal of methyl 3-[4-(indan-2-yloxy)-3-(1-methyl-1H-indazol-5-yl)-5-nitrophenyl]propionate according to claim 1, as an active ingredient; and
a dry pharmaceutically acceptable carrier.

3. A method of producing a crystal of methyl 3-[4-(indan-2-yloxy)-3-(1-methyl-1H-indazol-5-yl)-5-nitrophenyl]propionate according to claim 1, the method comprising:
adding any one or two or more solvents selected from the group consisting of heptane, diisopropyl ether, isopropanol, t-butyl methyl ether and water, to a solution of methyl 3-[4-(indan-2-yloxy)-3-(1-methyl-1H-indazol-5-yl)-5-nitrophenyl]propionate dissolved in any one or two or more solvents selected from the group consisting of toluene, ethyl acetate, tetrahydrofuran, acetone, dimethoxyethane and methanol, thus to produce crystals.

4. The crystal according to claim 1, wherein the crystal exhibits characteristic peaks at 2θ of 7.6±0.2°, 15.3±0.2°, 16.3±0.2°, 18.0±0.2°, 20.4±0.2°, 21.3±0.2°, 23.0±0.2°, 26.9±0.2° and 30.5±0.2°.

5. A crystal of methyl 3-[4-(indan-2-yloxy)-3-(1-methyl-1H-indazol-5-yl)-5-nitrophenyl]propionate having an X-ray diffraction spectrum substantially in accordance with FIG. 1.

* * * * *